United States Patent [19]

Walshe

[11] Patent Number: 5,723,488

[45] Date of Patent: Mar. 3, 1998

[54] ANTIPARASITIC AGENTS

[75] Inventor: Nigel Derek Walshe, Sandwich, United Kingdom

[73] Assignee: Pfizer Inc., New York, N.Y.

[21] Appl. No.: 687,435

[22] PCT Filed: Feb. 1, 1995

[86] PCT No.: PCT/EP95/00383

§ 371 Date: Aug. 12, 1996

§ 102(e) Date: Aug. 12, 1996

[87] PCT Pub. No.: WO95/22552

PCT Pub. Date: Aug. 24, 1995

[30] Foreign Application Priority Data

Feb. 16, 1994 [GB] United Kingdom ............ 9402916

[51] Int. Cl.$^6$ .................................................. A61K 31/335
[52] U.S. Cl. .................... 514/450; 514/30; 549/264; 536/7.1
[58] Field of Search ................ 549/264; 536/7.1; 514/30, 450

[56] References Cited

U.S. PATENT DOCUMENTS

| | | | |
|---|---|---|---|
| 4,423,209 | 12/1983 | Mrozik | 536/7.1 |
| 5,073,567 | 12/1991 | Kojima | 514/450 |
| 5,240,915 | 8/1993 | Rosegay | 514/30 |

FOREIGN PATENT DOCUMENTS 9318041  9/1993  WIPO.

*Primary Examiner*—Amelia Averill Owens
*Attorney, Agent, or Firm*—Peter C. Richardson; Gregg C. Benson; Robert T. Ronau

[57] ABSTRACT

A compound of formula (I):

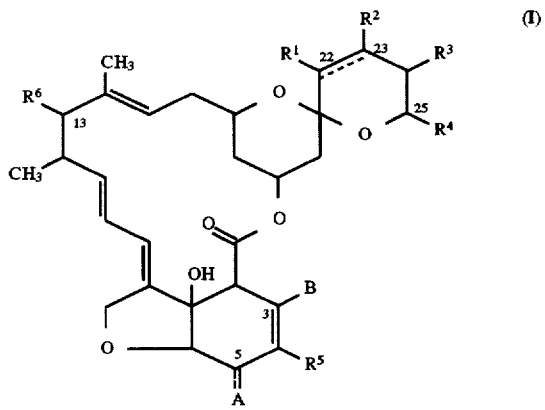

wherein the broken lines represent independently optional bonds, $R^1$ and $R^2$ being absent when the $C_{22}$–$C_{23}$ double bond is present.

20 Claims, No Drawings

ANTIPARASITIC AGENTS

This invention relates to antiparasitic agents and in particular to compounds related to the avermectins and milbemycins but having substituents at the 3-position.

The avermectins are a group of broad-spectrum antiparasitic agents referred to previously as the C-076 compounds. They are produced by fermenting a certain strain of microorganism *Streptomyces avermitilis* in an aqueous nutrient medium. The preparation and structure of these compounds obtained by fermentation are described in British Patent Specification 1573955. The milbemycins are structurally related macrolide antibiotics lacking the sugar residues at the 13-position. They may be produced by fermentation, for example as described in British Patent Specification No. 1390336 and European Patent Specification No. 0170006.

In addition to these fermentation-derived products, a large number of publications describe compounds derived semisynthetically from these products, many of which possess useful antiparasitic properties. Some of this chemistry is reviewed in *Macrolide Antibiotics*, Omura S., Ed., Academic Press, New York (1984) and by Davies, H. G. and Green, R. H. in *Natural Product Reports* (1986), 3, 87–121 and in *Chem. Soc. Rev.* (1991), 20, 211–269 and 271–239.

Compounds related to the original C-076 avermectins have also been prepared by fermentation of avermectin-producing micro-organism: For example European Patent Specifications 021473 and 0317148 describe production of compounds related to the C-076 avermectins but having a different substituent at the 25-position by fermentation in the present, in the fermentation medium, of certain acids.

Other publications mentioning different combinations of substituents at various positions on the avermectin or milbemycin nucleus are EP-A-317148, 340932, 350187, 410165, 259779 and 254583; DE-A-2329486 and GB-A-2166436.

B. J. Banks, in International Patent Application WO-A-9318041, describes the 3-substituted avermectin and milbemycin derivatives, where there is a 3,4-double bond and no 5-substituent.

The avermectins and milbemycins and their derivatives have the structure:

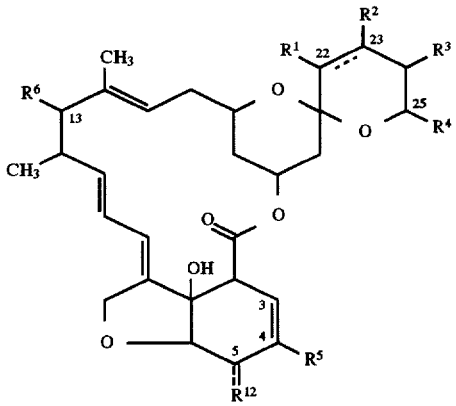

wherein the broken lines represent independently optional bonds, $R^1$ and $R^2$ being absent when the C22–C23 bond is present, $R^1$, $R^2$, $R^6$ and $R^{12}$ are independently H, OH, halo, oxo, oximino or an organic radical, $R^4$ and $R^5$ are organic radicals, and $R^3$ is H or an organic radical.

These compounds include the avermectins themselves and their substituted derivatives in which $R^6$ is a 4'-(a-L-oleandrosyl)-a-L-oleandrosyloxy group, optionally substituted at the 4" position; the avermectin monosaccharides and their derivatives in which $R^6$ is a-L-oleandrosyloxy, optionally substituted at the 4' position; the avermectin aglycones and their derivatives in which $R^6$ is OH or a substituent other than oleandrosyl replacing this group, and the milbemycins and their derivatives in which $R^6$ is H.

All the avermectins and structurally related milbemycins and their derivatives hitherto reported do not have a substituent at the 3-position when the double bond is in the C3–C4 position and with a 5-substituent, neither has any process capable of producing such compounds been reported.

It has now been discovered that avermectin and milbemycin derivatives having a wide range of substituents at the 3-position may be prepared and that some of these compounds have outstanding antiparasitic properties.

Compounds of the invention are of formula (I):

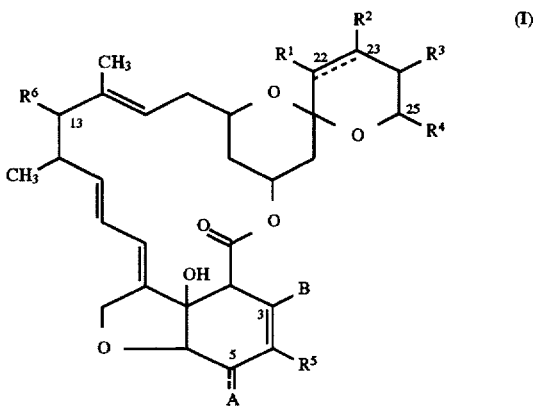

wherein the broken lines represent independently optional bonds, $R^1$ and $R^2$ being absent when the C22–C23 double bond is present, $R^1$, $R^2$, $R_6$ are independently H, OH, halo, oxo, oximino, or an organic radical, $R^4$ and $R^5$ are organic radicals, $R^1$ is H or an organic radical, A is OH, halo, $C_1$–$C_8$ alkoxy, $C_1$–$C_9$ alkanoyloxy, oxo, or oximino optionally substituted by a $C_1$–$C_8$ alkyl, alkenyl, alkynyl, aryl, trialkylsilyl, aralkyl, $C_1$–$C_9$ alkanoyl group or other group capable of being hydrolysed in vivo to the oxime, or hydrazono optionally substituted by at least one $C_1$–$C_8$ alkyl, alkenyl, alkynyl, aryl, trialkylsilyl, aralkyl, $C_1$–$C_9$ alkoxycarbonyl, carbamoyl, thiocarbamoyl, aroyl or $C_1$–$C_9$ alkanoyl group:

B is halo, $C_1$–$C_8$ alkyl, $C_1$–$C_8$ alkenyl, $C_1$–$C_8$ alkynyl, aryl, heteroaryl, $C_1$–$C_8$ alkanoyl, $C_1$–$C_8$ alkoxy, $C_1$–$C_9$ alkanoyloxy, $C_1$–$C_9$ alkoxycarbonyl, carboxy, arylcarbonyl, heteroaryl-carbonyl, mercapto, alkylthio, alkenylthio, arylthio, alkanoylthio, heteroarylthio, nitro, haloalkyl such as trifluoromethyl, hydroxyalkyl, alkoxyalkyl, mercaptoalkyl, alkylthio-alkyl, aminoalkyl optionally N-mono- or disubstituted by $C_1$–$C_8$ alkyl, $C_1$–$C_8$ alkenyl, $C_1$–$C_8$ alkynyl, $C_1$–$C_8$ alkanoyl, aryl, heteroaryl, $C_1$–$C_9$ alkoxycarbonyl, carboxy, arylcarbonyl, or by heteroarylcarbonyl, or B is hydroseleno, alkylseleno, arylseleno, heteroarylseleno, azido, or a cyclic ether group having up to 8 carbon atoms, said group optionally being substituted by at least one substituent selected from cyano, $C_1$–$C_8$ alkoxy, $C_1$–$C_8$ hydroxyalkyl, $C_1$–$C_9$ alkoxycarbonyl, aminocarbonyl, $C_1$–$C_9$ alkanoyl, arylcarbonyl, heteroarylcarbonyl, halo, haloalkyl and trialkylsilyloxyalkyl.

Compounds according to the invention include those in which the C5-A and C22-C23 optional bonds are independently present and those in which these optional bonds are independently absent (i.e. a single bond); $R^2$ is H, OH, $C_1-C_8$ alkoxy optionally substituted by halo or by $C_1-C_4$ alkoxy, $C_1-C_5$ alkanoyl, $C_1-C_5$ alkoxycarbonyl, carboxy, mercapto or by aryl, or $R^2$ is $C_3-C_8$ alkenyloxy, $C_1-C_9$ alkylcarbonyloxy or $C_3-C_9$ alkenylcarbonyloxy, arylcarbonyl or carbamoyl optionally substituted by a $C_1-C_9$ alkyl group, or $R^2$ is attached to the remainder of the molecule by a double bond and is oxo or oximino optionally O-substituted by a $C_1-C_8$ alkyl, alkenyl, alkynyl, trialkylsilyl, aryl or aralkyl group, or is methylene optionally substituted by a cyano or $C_1-C_9$ alkyl group; $R^1$ is H, OH or $C_1-C_8$ alkoxy or $C_1-C_9$ alkanoyloxy, or is attached to the remainder of the molecule by a double bond and is $=CH_2$, oxo or oximino optionally substituted as above $R^4$ is (a) an alpha-branched $C_3-C_8$ alkyl, alkenyl (including but-2-enyl, pent-2-enyl, and 4-methylpent-2-enyl), alkoxy-alkyl, or alkylthioalkyl group; an alpha-branched $C_4-C_8$ alkynyl group; a ($C_4-C_8$)cycloalkyl-alkyl group wherein the alkyl group is an alpha-branched $C_1-C_5$ alkyl group; a $C_3-C_8$ cycloalkyl or $C_5-C_8$ cycloalkenyl group, either of which may optionally be substituted by methylene or one or more $C_1-C_4$ alkyl groups or halo atoms; or a 3 to 6 membered oxygen or sulphur containing heterocyclic ring which may be saturated, or fully or partially unsaturated and which may optionally be substituted by one or more $C_1-C_4$ alkyl groups or halo atoms; or (b) a group of the formula —$CH_2R^8$ wherein $R^8$ is H, $C_1-C_8$ alkyl, $C_2-C_8$ alkenyl, $C_1-C_8$ alkynyl, alkoxy-alkyl or alkylthioalkyl containing from 1 to 6 carbon atoms in each alkyl or alkoxy group, wherein any of said alkyl, alkoxy, alkenyl or alkynyl groups may be substituted by one or more halo atoms; or a $C_3-C_8$ cycloalkyl or $C_5-C_8$ cycloalkenyl group, either of which may optionally be substituted by methylene or one or more $C_1-C_4$ alkyl groups or halo atoms; or a 3 to 6 membered oxygen or sulphur containing heterocyclic ring which may be saturated, or partially unsaturated and which may optionally be substituted by one or more $C_1-C_4$ alkyl groups or halo atoms; or a group of the formula $SR^9$ wherein $R^9$ is $C_1-C_8$ alkyl, $C_1-C_8$ alkenyl, $C_3-C_8$ alkynyl, $C_3-C_8$ cycloalkyl, $C_5-C_8$ cycloalkenyl, phenyl or substituted phenyl wherein the substituent is $C_1-C_4$ alkyl, $C_1-C_4$ alkoxy or halo; or a 3 to 6 membered oxygen or sulphur containing heterocylic ring which may be saturated, or fully or partially unsaturated and which may optionally be substituted by one or more $C_1-C_4$ alkyl groups or halo atoms; or (c) a $C_1-C_6$ alkyl group substituted by one oxo or one or more hydroxy groups or by a single oxygen atom on two adjacent carbon atoms forming an oxirane ring, or $R^4$ is a $C_1-C_5$ alkyl group substituted by a ($C_1-C_6$) alkoxy-carbonyl group, said substituents on $R^4$ being attached to either or both of a terminal carbon atom and a carbon atom adjacent a terminal carbon atom of $R^4$; or (d) $=CH_2$ or a group of the formula:

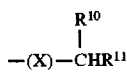

wherein $R^{10}$ and $R^{11}$ are both H; $R^{10}$ is H and $R^{11}$ is $C_1-C_3$ alkyl, or one of $R^{10}$ and $R^{11}$ is H and the other is phenyl, heteroaryl, $C_1-C_6$ alkoxycarbonyl or substituted phenyl or heteroaryl wherein said substituent is fluorine, chlorine, $C_1-C_4$ alkyl, $C_1-C_4$ alkoxy, $C_1-C_4$ alkylthio, hydroxy($C_1-C_4$)alkyl, cyano, aminosulphonyl, $C_1-C_6$ alkanoyl, $C_1-C_6$ alkoxycarbonyl, nitro, trifluoromethyl, trifluoromethoxy, amino or mono or di($C_1-C_4$) alkylamino; and X is a direct bond or is an alkylene group having from 2 to 6 carbon atoms which may be straight or branched-chain; or (e) phenyl which may optionally be substituted with at least one substituent selected from $C_1-C_4$ alkyl, $C_1-C_4$ alkylthio groups, halo atoms, trifluoromethyl, and cyano;

or $R^4$ may be a group of formula (II):

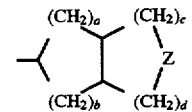

wherein Z is O, S or —$CH_2$— and a, b, c and d may each independently be 0, 1 or 2; the sum of a, b, c, and d not exceeding 5. $R^6$ may be hydrogen, hydroxy, $C_1-C_8$ alkoxy or alkenoxy, $C_1-C_9$ alkanoyloxy or alkenoyloxy, aroyloxy, oxymethyleneoxy-($C_1-C_5$) alkyloxy-($C_1-C_5$)alkyl, halogen, oxo, or optionally substituted oximino, hydrazono, carbazido or semicarbazido, N-($C_1-C_4$)alkyl semicarbazido, N,N-di($C_1-C_4$) alkylsemicarbazido, $C_1-C_5$ alkanoylhydrazido, benzoylhydrazido or ($C_1-C_4$) alkyl benzoylhydrazido; or $R^6$ may be a group capable of being hydrolysed in vivo to give OH; or $R^6$ may be

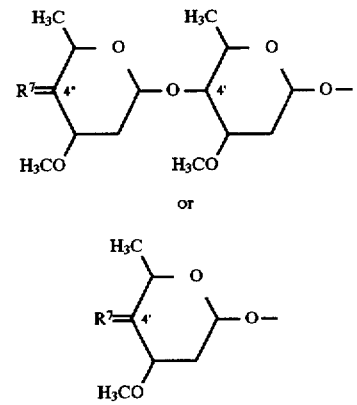

wherein $R^7$ is attached to C-4" or C-4' by a single bond and is hydroxy, $C_1-C_9$ alkanoyloxy or alkenoyloxy, aroyloxy, $C_1-C_8$ alkoxy, amino, N-($C_1-C_8$)alkylamino, N,N-di($C_1-C_9$)alkylamino, N-($C_1-C_5$)alkanoylamino, or N,N-di($C_1-C_9$)alkanoylamino; or $R^7$ is attached to C-4" or C-4' by a double bond and is oxo, optionally substituted oximino, semicarbazido, N-($C_1-C_4$) alkylsemicarbazido, N,N-di($C_1-C_4$) alkylsemicarbazido, ($C_1-C_5$)alkanoylhydrazido, benzoylhydrazido, or ($C_1-C_4$)alkylbenzoylhydrazido;

or $R^7$ is a group capable of being hydrolysed in vivo to give OH.

$R^3$ may be H or $C_1-C_6$ alkyl $R^5$ may be methyl, hydroxymethyl, ($C_1-C_4$ alkoxy)-methyl, ($C_1-C_5$ alkanoyl) oxymethyl, ($C_1-C_5$ alkenoyl)

-oxymethyl, aroyloxymethyl, aralkanoyloxymethyl, formyl.optionally substituted oximino, halomethyl, azidomethyl or cyanomethyl.

Compounds of the invention include those in which $R^2$ is H, OH, O-($C_1$-$C_4$)alkyl, O-($C_1$-$C_5$)alkanoyl, oxo and oximino optionally substituted by $C_1$-$C_4$ alkyl or aryl ($C_1$-$C_4$)alkyl; those in which $R^4$ is straight or branched-chain alkyl, alkenyl, cycloalkyl or cycloalkenyl (including methyl, ethyl, 2-propyl, 2-butyl, 2-buten-2-yl, 2-penten-2-yl, 4-methyl-2-penten-2-yl and cyclohexyl); those in which $R^1$ is H, OH, oxo or oximino; and those in which $R^6$ is H or is of formula:

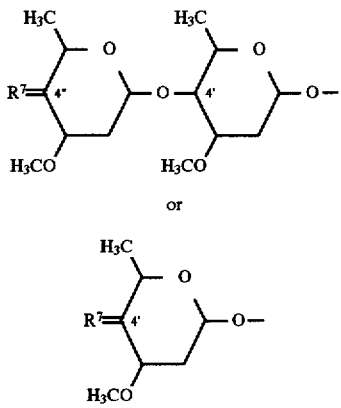

where $R^7$ is OH, ($C_1$-$C_4$)alkoxy, ($C_1$-$C_5$) alkanoyloxy, amino, N-($C_1$-$C_4$)alkylamino, N-($C_1$-$C_5$)alkanoylamino, oxo or oximino optionally substituted by a $C_1$-$C_4$ alkyl group.

In preferred compounds of the invention B is halo (such as chloro, bromo or iodo), alkyl, alkoxyalkyl, acylalkenyl or acyl; A is hydroxy or oximino; $R^6$ is H, OH, α-L-oleandroxyloxy or $4^1$-(α-L-oleandrosyl)-α-L-oleandrosyloxy; $R^1$ is H and $R^2$ is H, OH, or methoxy, or $R^1$ and $R^2$ are both absent and the $C_{22}$–$C_{23}$ bond is single or double. Particular compounds are identified in the Examples below.

In all the above definitions, unless the context requires otherwise, alkyl groups containing 3 or more carbon atoms may be straight or branched-chain; halo means fluoro, chloro, bromo or iodo; alkenyl groups containing 3 or more carbon atoms may be straight or branched-chain, optionally substituted by one or more functional groups including cyano, alkoxycarbonyl, aminocarbonyl, alkanoyl, arylcarbonyl, heteroaryl-carbonyl, halo, haloalkyl such as trifluoromethyl, alkynyl groups containing 3 or more carbon atoms may be straight or branched-chain, optionally substituted by one or more functional groups including cyano, alkoxy-carbonyl, aminocarbonyl, alkanoyl, arylcarbonyl, heteroarylcarbonyl, halo, haloalkyl such as trifluoromethyl; aryl means phenyl optionally substituted by one or more $C_1$-$C_4$ alkyl, $C_1$-$C_4$ alkoxy groups, nitro groups or halo atoms; and heteroaryl means aromatic heterocycle optionally substituted by one or more $C_1$-$C_4$ alkyl or $C_1$-$C_4$ alkoxy groups, nitro groups or halo atoms.

Compounds of the invention include avermectins and corresponding monosaccharides and aglycones, and milbemycins.

It will be understood that the compounds of the invention include several asymmetric centres and accordingly may exist as several pairs of stereoisomers. The invention includes all such stereoisomers, whether separated or not.

Compounds of formula (I) as defined above may be made by a method which comprises:

(a) allowing a compound of formula (I) but in which B is H and A is =O to react with hydrazine optionally substituted by at least one $C_1$-$C_8$ alkyl, alkenyl, aryl, trialkylsilyl, aralkyl, $C_1$-$C_9$ alkoxycarbonyl, carbamoyl, thiocarbamoyl, aroyl or $C_1$-$C_9$ alkanoyl group to yield a compound of formula (I) in which A is optionally substituted hydrazono.

(b) allowing the hydrazone so obtained to react with a source of electrophilic species $E^⊕$ where $E^⊕$ is $Cl^⊕$, $Br^⊕$, $I^⊕$, $NO_2^⊕$, $ArS^⊕$ or $ArSe^⊕$ where Ar is an aryl group or $E^⊕$ is an iminium ion to yield a compound of formula (I) in which B is Cl, Br, I, $NO_2$, ArS, ArSe or an optionally substituted aminoalkyl group respectively.

(c) if desired, allowing the compound produced from (b) in which B is Cl, Br or I to react with a stannane comprising an optionally substituted alkyl, alkenyl, alkynyl, aryl or heterocyclic substituent, in the presence of a catalyst such as triphenylphosphine palladium, to give a compound of formula (I) in which B is an optionally substituted alkyl, alkenyl, alkynyl, aryl or heterocyclic substituent respectively.

(d) if desired, allowing the compound produced from (b) in which B is Cl, Br or I to react with an azide to produce a compound of formula (I) in which B is $N_3$.

(e) if desired, oxidising a compound from (c) in which B is alkenyl to produce a compound of formula (I) in which B is a cyclic ether group.

(f) if desired, treating a compound from (b) in which B is ArS or ArSe with a thiol or hydroselenide other than ArSH or ArSeH to produce a compound of formula (I) in which B is a mercapto or hydroselenide group, and if desired allowing the product to react with an alkyl, alkenyl, aryl, alkanoyl or heteroaryl halide.

When the electrophilic species is $Cl^⊕$ the source thereof may be N-chlorosuccinimide or N-chlorobenzotriazole. N-iodosuccinimide and N-bromosuccinimide are possible sources of $I^⊕$ and $Br^⊕$ respectively and tetranitromethane of $NO_2^⊕$. Dinitrophenylsulphenyl chloride may be used as the source of $ArS^⊕$, and N-phenylselenophthal imide for $ArSe^⊕$. The aminoalkyl group may be derived from Eschenmoser's salt ($Me_2$ N—$CH_2^⊕$ $Cl^⊖$).

Methods of preparation of compounds of the invention are exemplified in Schemes I and II below, where "$E^+$" is an electrophile, "$N^-$" is a nucleophile and Y is an organic radical. A wide variety of compounds is thus accessible.

No such chemistry has been reported in the structurally complex avermectin and milbemycin field.

In Scheme I, the 5-ketone is converted to the hydrazone (III) using 1,1-dimethylhydrazine, for example in dichloromethane under acidic conditions. Other hydrazines with an unsubstituted terminus may be used in place of 1,1-dimethylhydrazine to produce other substituted hydrazones. Compound (III) may then be reacted with an electrophile $E^+$, such as $Cl^+$(from N-chlorosuccinimide, in acetonitrile for example), to give compounds of formula (IV).

The hydrazone moiety may be further manipulated, for example as shown in Scheme II, into either a ketone (for example by acid-catalysed hydrolysis), an oxime (for example by reaction with hydroxylammonium chloride in a mixed solvent), or an alcohol (for example via a ketone produced by reaction with copper (II) acetate in aqueous acetic acid, followed by reaction with sodium borohydride in methanol).

SCHEME I

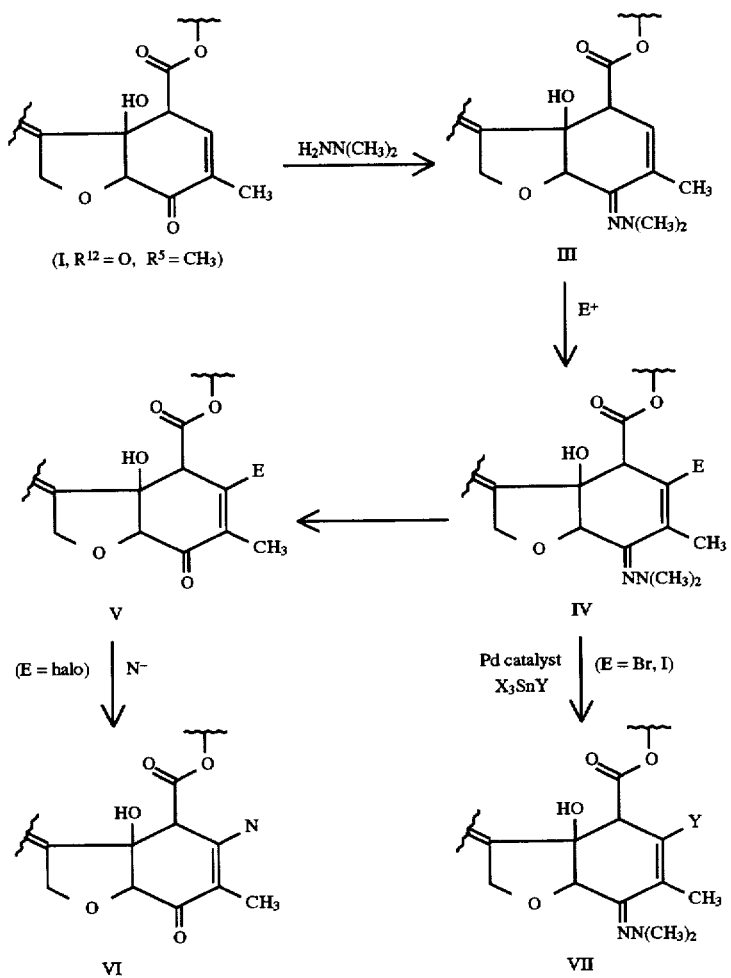

SCHEME II

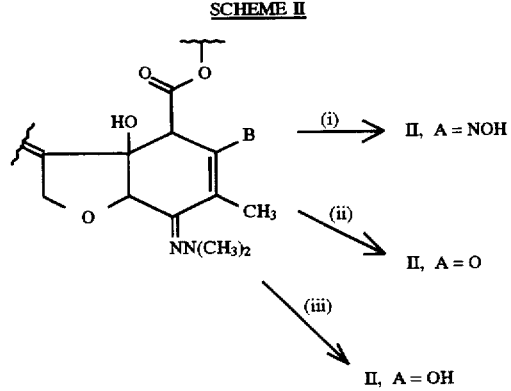

(i) Hydroxylammonium chloride, dioxan, methanol, water
(ii) Acetic acid, tetrahydrofuran, water, sodium acetate
(iii) (a) Copper (II) acetate, acetic acid, water,
    (b) sodium borohydride, methanol In Scheme I, the "E" moiety of compound (V) may be displaced by a nucleophile "N⁻", or an organic radical Y (for example, by the "Stille coupling", of a 3-iodo compound of formula V with a vinylstannane, catalysed by a palladium (O) species, and in a solvent such as dimethylformamide), to give compounds of formula VI or VII.

The starting materials of formula (I) comprising different combinations of substituents $R^1$–$R^6$ and $R^{12}$, may generally be made by methods known in the art and discussed in the above-mentioned publications. In particular, 5-ketones can be made from corresponding avermectins and milbemycins using manganese dioxide oxidations (see for example *J. Agric. Food Chem.*(1981)29, 884–886). It is believed that the above-described method of the invention is applicable to all starting compounds of formula (I) in which substituents $R^1$–$R^6$ are compatible with the reagents used. However in some instances it may be necessary or desirable to replace some of the $R^1$–$R^6$ substituents with other substituents after conversion of the formula (I) starting material to the 3-substituted compounds. For example, when a compound of formula (I) in which $R^6$ is $4^1$-(α-L-oleandrosyl)-α-L oleandrosyloxy (i.e. a disaccharide) is obtained, it may be reduced to the monosaccharide (in which $R^6$ is α-L-oleandrosyloxy) or to the aglycone (in which $R^6$ is —OH) by hydrolysis using an acid such as sulphuric acid. When $R^1$ and $R^2$ are absent a double bond at the 22–23 position may be hydrogenated to produce a 22,23-dihydro derivative in which $R^1$ and $R^2$ are both H. Other conversions of substituent groups $R^1$–$R^6$ of the compounds of formula I as defined above may be performed by methods known in the avermectin and milbemycin art.

The compounds of the invention are highly active antiparasitic agents. Thus the compounds are effective in treating a variety of conditions caused by ecto- and endoparasites including, in particular, fleas. The compounds are also of value in treating other ectoparasite infections including in particular arthropod ectoparasites of humans, animals and birds such as ticks, mites, lice, blowfly, biting insects and migrating dipterous larvae which can affect cattle and horses. The compounds can also be used to treat helminthiasis which is most frequently caused by a group of parasitic worms described as nematodes and which can cause severe economic losses in swine, sheep, horses and cattle as well as affecting domestic animals and poultry. The compounds are also effective against other nematodes which affect various species of animals including, for example, Dirofilaria in dogs and various parasites which can infect animals and humans including gastro-intestinal parasites such as Ancylostoma, Necator, Ascaris, Strongyloides, Trichinella, Toxocara, Capillaria, Trichuris, Enterobius and parasites which are found in the blood or other tissues and organs such as filiarial worms and the extra-intestinal stages of Strongyloides, Trichinella and Toxocara.

The compounds of formula (I) may be administered as a formulation appropriate to the specific use envisaged and to the particular species of host animal being treated and the parasite or insect involved. For use as an insecticide and for treating agricultural pests the compounds are applied as sprays, dusts, pour-on formulations, emulsions and the like in accordance with standard agricultural practice.

For human use the compounds are administered as a pharmaceutically acceptable formulation in accordance with normal medical practice.

The compounds are also useful against insect pests of stored grains such as *Tribolium sp., Tenebrio sp.*, and of agricultural plants such as spider mites, (*Tetranychus sp.*) aphids, (*Acyrthiosiphon sp.*), against migratory orthopterans such as locusts and immature stages of insects living on plant tissue. The compounds are useful as nematocides for the control of soil nematodes and plant parasites such as *Meloidogyne sp.* which may be of importance in agriculture. The compounds are active against other plant pests such as the southern army worm and Mexican bean beetle larvae.

For use as insecticides the compounds are applied as sprays, dusts, emulsions, pour-on formulations and the like in accordance with standard veterinary practice.

For use as an anthelmintic the compounds may be administered by injection, either subcutaneously or intramuscularly, alternatively they may be administered orally in the form of a capsule, bolus, tablet, chewable tablet or liquid drench, or they may be administered as a topical formulation or as an implant. For topical application dip, spray, powder, dust, pour-on, spot-on, jetting fluid, shampoos, collar, tag or harness may be used. Such formulations are prepared in a conventional manner in accordance with standard veterinary practice. Thus capsules, boluses or tablets may be prepared by mixing the active ingredient with a suitable finely divided diluent or carrier, additionally containing a disintegrating agent and/or binder such as starch, lactose, talc, or magnesium stearate. A drench formulation may be prepared by dispersing the active ingredient in an aqueous solution together with dispersing or wetting agents and injectable formulations may be prepared in the form of a sterile solution or emulsion. Pour-on or spot-on formulations may be prepared by dissolving the active ingredient in an acceptable liquid carrier vehicle, such as butyl digol, liquid paraffin or non-volatile ester with or without addition of a volatile component such as isopropanol. Alternatively, pour-on, spot-on or spray formulations can be prepared by encapsulation to leave a residue of active agent on the surface of the animal. These formulations will vary with regard to the weight of active compound depending on the species of host animal to be treated, the severity and type of infection and the body weight of the host. The compounds may be administered continuously, particularly for prophylaxis, by known methods. Generally for oral, parenteral and pour-on administration a dose of from about 0.001 to 10 mg per kg of animal body weight given as a single dose or in divided doses for a period of from 1 to 5 days will be satisfactory but of course there can be instances where higher or lower dosage ranges are indicated and such are within the scope of this invention. As an alternative the compounds may be administered with the animal feedstuff and for this purpose a concentrated feed additive or premix may be prepared for mixing with the normal animal feed.

The invention is illustrated by the following Examples, in which "avermectin B2" refers to an avermectin having an OH substituents at the 5-and 23-position and a single bond at the 22–23 position, "avermectin B1" refers to an avermectin having a double bond at the 22–23 position and an OH substituent at the 5-position, and "avermectin A1" is as for avermectin B1 but having a methoxy group at the 5-position. The 5-ketone starting compounds were prepared as described in International Patent Application WO 94/15944.

PREPARATION A 22,23-Dihydro-25-cyclohexyl avermectin B1 monosaccharide 5-N,N-dimethylhydrazone 5-Keto-22,23-dihydro-25-cyclohexyl avermectin B1 monosaccharide (1 g) was dissolved in dichloromethane (100 ml) and N,N-dimethylhydrazine (2 g) and acetic acid (10 ml) added. The reaction was stirred at room temperature for 24 hours. It was then washed well with water, aqueous sodium bicarbonate and brine and then dried (MgSO$_4$). Evaporation gave a brown gum which was chromatographed over silica gel (100 g) and eluted with ether:hexane (1:1). Appropriate fractions were pooled and evaporated to give the title product (660 mg).

EXAMPLE 1

3-Chloro-22,23-dihydro-25-cyclohexyl avermectin B1 monosaccharide 5-N,N-dimethylhydrazone The hydrazone from Preparation A (200 mg) was dissolved in acetonitrile (40 ml) kept at 0°. N-Chlorosuccinimide (200 mg) was added, and the mixture kept at 0° for 18 hours. Tlc (thin layer chromatography) showed the reaction was approaching completion, so the mixture was poured into water (150 ml) containing sodium metabisulphite (0.5 g). It was extracted with ether (100 ml×2), and the extracts washed with water and brine and dried (MgSO$_4$). Evaporation gave a gum which was chromatographed over silica gel (80 g) and eluted with dichloromethane:ether (1:2). Appropriate fractions were collected and pooled. The product was characterized by nmr and mass spectroscopy.

EXAMPLE 2

3-Chloro-5-keto-22,23-dihydro-25-cyclohexyl avermectin B1 monosaccharide

The 3-chloro-hydrazone from Example 1 was dissolved in a mixture of acetic acid, tetrahydrofuran, water and sodium acetate (5:2:2:1) (100 ml), and stood at room temperature for 1 week. The reaction was then diluted with water (200 ml) and extracted with ether (2×75 ml portions). The ethereal extracts were washed with water (2×100 ml), saturated sodium bicarbonate solution, and brine. The ether was then dried (MgSO$_4$) and evaporated to give a gum. This was chromatographed over silica gel and elued ether:hexane (1:1). The desired ketone was eluted first. It was characterized by nmr, mass and infrared spectroscopy.

EXAMPLE 3

3-Chloro-22,23-dihydro-25-cyclohexyl avermectin B1 monosaccharide

The ketone from Example 2 (20 mg) was dissolved in methanol (2 ml) and sodium borohydride (10 mg) added. After standing for 30 minutes at room temperature, the mixture was poured into semi-saturated brine (30 ml) and extracted with ether (2×20 ml). The extracts were washed with brine and dried (MgSO$_4$). The residue was purified on a 1" Dynamax (TM) ODS column, eluting with methanol:water (90:10) at 20 ml/min. The product was characterized by nmr and mass spectroscopy.

EXAMPLE 4

3-Chloro-22,23-dihydro-25-cyclohexyl avermectin B1 monosaccharide 5-oxime

The ketone from Example 2 (50 mg) was dissolved in a mixture of methanol (4 ml) and dioxan (1 ml), and hydroxylammonium chloride (50 mg) added. This was stirred at room temperature overnight, when a further 50 mg of the hydroxylamine salt was added. After 4 hours, a further 100 mg of the hydroxylamine salt was added, and the mixture stirred for 2 hours. The reaction was then poured into semisaturated brine (50 ml) and extracted with ether (2×100 ml). Extracts were dried (MgSO$_4$), and evaporated to a gum. This was purified on a 1" Dynamax ODS column, eluting methanol:water (90:10) at 20 ml/min. The product was characterized by mass and nmr spectroscopy.

EXAMPLE 5

3-[2,4-Dinitrophenylthio]-22,23-dihydro-25-cyclohexyl avermectin B1 monosaccharide 5-N,N-dimethylhydrazone The hydrazone from Preparation A (200 mg) was dissolved in acetonitrile (20 ml), cooled to 0°, and calcium carbonate (200 mg) added. Next, 2,4-dinitrobenzenesulphenyl chloride (200 mg) was added all at once. The mixture was kept at 0° overnight. It was then poured into water (100 ml) and extracted with ether (2×75 ml). The extracts were washed with saturated sodium bicarbonate solution, and brine. They were dried (MgSO$_4$) and evaporated to an orange foam. This was chromatographed over silica gel (90 g) and eluted with dichloromethane:ether (2:1). The bright orange-yellow band which eluted was collected. The structure was confirmed by mass and nmr spectroscopy.

EXAMPLE 6

3-[2,4-Dinitrophenylthio]-22,23-dihydro-25-cyclohexyl avermectin B1 monosaccharide 5-oxime The compound from Example 5 (1.2 g) was dissolved in a mixture of dioxan and methanol (240 ml of 1:1) and a solution of hydroxylammonium chloride (10 g) in water (60 ml) added. The solution was stirred at room temperature for 2 days, when all starting reagents had disappeared. It was then partitioned between water and ether, the organic phase was washed with water and brine, dried (MgSO$_4$) and evaporated to give a yellow gum. This was chromatographed over silica gel, eluting with ether:hexane (2:1). Appropriate fractions were collected and evaporated to give the title compound (800 mg), characterized by mass and nmr spectroscopy.

EXAMPLE 7

3-[2,4-Dinitrophenylthio]-22,23-dihydro-25-cyclohexyl avermectin B1 monosaccharide The product from Example 5 (100 mg) was dissolved in acetic acid (10 ml) and a solution of copper(II) acetate (400 mg) in water (5 ml) added. The reaction was stirred at room temperature for 1 week. It was then partitioned between ethyl acetate (50 ml) and water (50 ml), the organic phase washed with water and saturated sodium bicarbonate solution, dried (MgSO$_4$) and evaporated to a yellow foam. Comprising the 5-ketone. This was dissolved in methanol (50 ml) and sodium borohydride (20 mg) added. After 5 minutes, the reaction was quenched with aqueous citric acid and extracted with ethyl acetate. The organic phase was washed with water and brine, dried and evaporated to an orange glass. This was chromatographed over silica gel (30 g), and eluted with ether:dichloromethane (3:1). An orange band eluted first, which was discarded, followed by the title compound (20 mg), which was characterized by mass and nmr spectroscopy.

EXAMPLE 8

3-Mercapto-22,23-dihydro-25-cyclohexyl avermectin B1 monosaccharide 5-N,N-dimethylhydrazone The sulphide from Example 5 (300 mg) was dissolved in dichloromethane (40 ml). Ethanethiol (5 ml) followed by triethylamine (3 ml) was added and the mixture stirred at room temperature for 3 hours. A further portion of triethylamine (1 ml) and ethanethiol (5 ml) was added and the mixture stirred for a further 8 hours. The volatiles were removed, and the resulting dark oil was chromatographed over silica gel, eluting with dichloromethane. A dark orange band eluted first, followed by the title compound, obtained on evaporation as orange crystals (200 mg). The compound was characterized by mass and nmr spectroscopy.

EXAMPLE 9

3-Methylthio-22,23-dihydro-25-cyclohexyl avermectin B1 monosaccharide 5-N,N-dimethylhydrazone The thiol from Example 8 (90 mg) was dissolved in ether (2 ml) and methyl iodide (1 ml) and Hunig's base (0.5 ml) added. After 6 hours, all starting reagents had gone. The volatiles were removed and the residue chromatographed over silica gel (50 g), and eluted with dichloromethane:ether (3:1). Fractions containing the less polar material were collected, and shown to contain the title compound, as proved by nmr and mass spectrometry.

EXAMPLE 10

3-Methylthio-22,23-dihydro-25-cyclohexyl avermectin B1 monosaccharide 5-oxime

The methylthio compound from Example 9 (40 mg) was dissolved in a mixture of methanol and dioxan (10 ml of 1:1). Hydroxylammonium chloride (0.5 g) in water (2 ml) was added. After 6 hours, reaction was incomplete and a further 2 g of the hydroxylamine salt added in water (2 ml). After 12 hours, the mixture was poured into water (50 ml) and extracted with ether (2×50 ml). The extracts were washed with brine and dried (MgSO$_4$). Evaporation gave a gum which was purified on a 1" Dynamax (TM) ODS column, eluting with methanol:water (90:10) at 20 ml/min. The structure was established by nmr and mass spectrometry.

EXAMPLE 11

3-Methylthio-22,23-dihydro-25-cyclohexyl avermectin B1 monosaccharide

The methylthio compound from Example 9 (50 mg) was dissolved in acetic acid (6 ml) and saturated aqueous copper (II) acetate solution (3 ml) added. This was stirred at 35° for 24 hours. The reaction was then diluted with water (50 ml) and extracted with ether (2×50 ml). The extracts were washed with water, saturated sodium bicarbonate solution and brine, dried (MgSO$_4$), and evaporated to a gum. This was the 5-ketone. This was dissolved in methanol (3 ml) and sodium borohydride (20 mg) added. After 30 minutes, the reaction was quenched with 5 ml of 10% aqueous citric acid, extracted with ether (2×50 ml), the ether dried (MgSO$_4$) and evaporated to a gum. This was purified on a 1" Dynamax (TM) ODS column, eluting with methanol:water (9:1) at 20 ml/min. Product was eluted after 22–24 minutes, and was characterized by mass and nmr spectroscopy.

EXAMPLE 12

3-Dimethylaminomethyl-22,23-dihydro-25-cyclohexyl avermectin B1 monosaccharide 5-N,N-dimethylhydrazone The hydrazone from Preparation A (70 mg) was dissolved in acetonitrile (10 ml). Calcium carbonate (70 mg), then Eschenmoser's salt (Me$_2$N-CH$_2^+$Cl$^-$) (100 mg) added. The mixture was stored at 0° for 24 hours. It was then poured onto saturated sodium bicarbonate solution (50 ml), and extracted with ether (2×75 ml). The organic phase was washed with water, brine, and dried (MgSO$_4$). Evaporation gave a gum. The product was then purified by chromatography over silica gel (50 g) and eluted ether:dichloromethane (1:1). Residual starting material eluted first, followed by the title compound, characterized by mass and nmr spectroscopy.

EXAMPLE 13

3-Dimethylaminomethyl-22,23-dihydro-25-cyclohexyl avermectin B1 monosaccharide 5-oxime The product from Example 12 (200 mg) was dissolved in a mixture of methanol and dioxan (40 ml of 1:1), and a solution of hydroxylammonium chloride (2 g) in water (10 ml) added. The reaction was left at room temperature for 3 hours, then overnight in the deep freeze. It was then partially evaporated to remove methanol, neutralized with excess sodium bicarbonate solution, the product extracted into ether (2×100 ml), washed with brine and dried (MgSO$_4$). Evaporation gave the product, which was purified by chromatography over silica gel (60 g), eluting with dichloromethane:ether 4:1. Appropriate fractions were pooled to give the title compound (96 mg), characterized by mass and nmr spectroscopy.

EXAMPLE 14

3-Phenylseleno-22,23-dihydro-25-cyclohexyl avermectin B1 monosaccharide 5-N,N-dimethylhydrazone The hydrazone from Preparation A (100 mg) was dissolved in acetonitrile (40 ml) and N-phenylselenophthalimide (100 mg) added. The solution was shaken until all material was dissolved, then kept at 0° for 48 hours. It was then poured into water (100 ml) and extracted with ether (2×150 ml). Extracts were washed with brine and dried (MgSO$_4$), and evaporated to a gum. This was chromatographed over silica gel (80 g) and eluted with dichloromethane:ether (3:1). Some phthalimide eluted first, then the title product, which was characterized by nmr and mass spectroscopy.

EXAMPLE 15

3-Phenylseleno-22,23-dihydro-25-cyclohexyl avermectin B1 monosaccharide 5-oxime The product from Example 14 (480 mg) was dissolved in 150 ml of a 1:1 methanol/dioxan mixture. A total of 5 g of hydroxylammonium chloride in water (30 ml) was added, and the reaction left for 24 hours at room temperature. It was then poured into water (500 ml) and extracted with ether (2×250 ml). The extracts were washed with water, brine and dried (MgSO$_4$). Evaporation gave a gum. This was chromatographed over silica gel (100 g) and eluted dichloromethane:ether (4:1). Fractions containing product were collected and combined. The title compound was characterized by nmr and mass spectroscopy.

EXAMPLE 16

3-Phenylseleno-22,23-dihydro-25-cyclohexyl avermectin B1 monosaccharide

The product from Example 14 (40 mg) was dissolved in acetic acid (20 ml) and saturated copper(II) acetate solution (7 ml) added. The reaction was left for 4 days at room temperature, then worked up as described in Example 7. The crude product (the 5-ketone) was dissolved in methanol (5 ml) and sodium borohydride (20 mg) added. After 20 minutes, the reaction was worked up as in Example 7, and the product purified on a 1" Dynamax (TM) ODS column, eluting with methanol:water (95:5) at 20 ml/min. The product eluted at 17 minutes and was characterized by nmr and mass spectroscopy.

EXAMPLE 17

3-Nitro-22,23-dihydro-25-cyclohexyl avermectin B1 monosaccharide 5-N,N-dimethylhydrazone The hydrazone from Preparation A (150 mg) was dissolved in acetonitrile (30 ml) and the solution cooled to 0°. Tetranitromethane (0.25 ml) was added, and the reaction kept for 12 hours at 0°. The acetonitrile was evaporated, and the residue chromatographed over silica gel (90 g), eluting with dichloromethane:ether (3:1). A fast-running yellow band was discarded, then 20 fractions of 20 ml collected. Fractions 5–6 contained the title compound, characterized by mass and nmr spectroscopy.

EXAMPLE 18

3-Iodo-22,23-dihydro-25-cyclohexyl avermectin B1 monosaccharide 5-N,N-dimethylhydrazone The hydrazone from Preparation A (50 mg) was dissolved in acetonitrile (20 ml) and the solution cooled to 0°.

15

N-Iodosuccinimide was added in three portions of 10 mg each over 3 days. The reaction was poured into water (50 ml), and extracted with ether (2×75 ml). The extracts were washed with brine and dried (MgSO$_4$). Evaporation gave a yellow gum, which was chromatographed over silica gel (50 g), eluting with dichloromethane:ether (3:1). Fractions containing product were collected. The title compound was characterized by mass and nmr spectroscopy.

EXAMPLE 19

3-Iodo-22,23-dihydro-25-cyclohexyl avermectin B1 monosaccharide

The iodo compound from Example 18 (50 mg) was dissolved in acetic acid (5 ml) and saturated copper(II) acetate solution (2 ml) added. The reaction was stirred at room temperature for 72 hours, then worked up as described in Example 7 to give the crude 5-ketone. This was reduced to the title compound using the method of Example 7, which was purified on a 1" Dynamax (TM) ODS column, eluting with methanol:water (9:1) at 9 ml/min. The product was characterized by nmr and mass spectroscopy.

EXAMPLE 20

3-Chloro-25-cyclohexyl avermectin B1 5-N,N-dimethylhydrazone

25-Cyclohexyl avermectin B1 5-N,N-dimethylhydrazone (4 g), prepared from the corresponding ketone according to the method of Preparation A, was dissolved in acetonitrile (800 ml), cooled to 0°, and N-chlorosuccinimide (4 g) and 4A molecular sieve (20 g) added. The reaction was left at 0° for 24 hours. The sieve was then filtered off, and the reaction worked up as in Example 1. The crude product was purified by chromatography over silica gel (200 g), eluting with dichloromethane:ether (4:1). The product was characterized by mass and nmr spectroscopy.

EXAMPLE 21

3-Chloro-25-cyclohexyl avermectin B1

The hydrazone from Example 20 (1.1 g) was dissolved in acetic acid (70 ml) and saturated copper(II) acetate (35 ml) added. The reaction was left at room temperature for 72 hours, then worked up as in Example 7 to give the crude 5-ketone. This was reduced with sodium borohydride using the protocol of Example 7, and the title compound purified on a 2" Dynamax (TM) ODS column in 2 batches, eluting with methanol:water (9:1) at 45 ml/min. It was characterized by nmr and mass spectroscopy.

EXAMPLE 22

3-Chloro-25-cyclohexyl avermectin B1 5-oxime

The hydrazone from Example 20 (0.3 g) was dissolved in a 1:1 mixture of methanol and dioxan (90 ml). Hydroxylammonium chloride (3 g) in water (20 ml) was added, and the mixture stood at room temperature for 16 hours. The reaction was worked up as in Example 4, and the crude product purified on a 1" Dynamax (TM) ODS column, eluting with methanol:water (95:5) at 9 ml/min. The title compound was characterized by mass and nmr spectroscopy.

EXAMPLE 23

3-Chloro-25-cyclohexyl avermectin B1 monosaccharide

The 3-chloroavermectin from Example 21 (50 mg) was dissolved in 1.5 ml of a 1% solution of sulphuric acid in isopropanol. The reaction was stirred at room temperature overnight. It was then partitioned between ether and saturated sodium bicarbonate solution, the organic phase was dried (MgSO$_4$) and evaporated. The crude product was purified on a 1" Dynamax (TM) ODS column, eluting with methanol:water (9:1) at 9 ml/min. The title compound was then characterized by nmr and mass spectroscopy.

EXAMPLE 24

3-Chloro-22,23-dihydro-25-cyclohexyl avermectin B1

The 3-chloro-avermectin from Example 21 (0.1 g) was dissolved in toluene (5 ml). The solution was sparged with nitrogen and degassed ultrasonically. Wilkinson's catalyst (20 mg) was added, and the mixture hydrogenated at a pressure of 50 p.s.i overnight. A further portion (20 mg) of catalyst was added, and hydrogenation continued for 24 hours. The reaction mixture was then filtered and evaporated to give a brown solid. This was dissolved in methanol, filtered and purified on a 1" Dynamax (TM) ODS column, eluting with methanol:water (9:1) at 9 ml/min. The title product was characterized by nmr and mass spectrometry.

EXAMPLE 25

3-Chloro-25-cyclohexyl avermectin B2

This was prepared from 25-cyclohexyl avermectin B2 5-N,N-dimethylhydrazone (synthesized from 5-keto-25-cyclohexyl avermectin B2 according to the method of Preparation A) via conversion to the 3-chloro-25-cyclohexyl avermectin B2 N,N-dimethylhydrazone, according to the method of Example 1. This was hydrolysed to the 5-ketone, as detailed in Example 7, and reduced to the title compound. This was characterized by nmr and mass spectroscopy.

EXAMPLE 26

3-Chloro-25-cyclohexyl avermectin B2 monosaccharide

This was prepared from the compound from Example 25, using the hydrolysis protocol described in Example 23. This was characterized by nmr and mass spectroscopy.

EXAMPLE 27

3-Chloro-25-cyclohexyl avermectin B2 5-oxime

This was prepared from 25-cyclohexyl avermectin B2 5-N,N-dimethylhydrazone (synthesized from 5-keto-25-cyclohexyl avermectin B2 according to the method of Preparation A) via conversion to the 3-chloro-25-cyclohexyl avermectin B2 N,N-dimethylhydrazone, as in Example 1. Oximation of this to the title compound was performed as described in Example 4. This was characterized by nmr and mass spectroscopy.

EXAMPLE 28

3-Chloro-23-O-methyl-25-cyclohexyl avermectin B2

This was prepared from 23-O-methyl-25-cyclohexyl avermectin B2 5-N,N-dimethylhydrazone (synthesized from 5-keto-23-O-methyl-25-cyclohexyl avermectin B2 according to the method of Preparation A) via conversion to the 3-chloro-23-O-methyl-25-cyclohexyl avermectin B2 N,N- dimethylhydrazone, as detailed in Example 1. This was hydrolysed to the 5-ketone, as in Example 7, and reduced to the title compound. This was characterized by nmr and mass spectroscopy.

EXAMPLE 29

3-Chloro-23-O-methyl-25-cyclohexyl avermectin B2 monosaccharide

This was prepared from the compound from Example 28, using the hydrolysis protocol described in Example 23. This was characterized by nmr and mass spectroscopy.

EXAMPLE 30

3-Chloro-23-O-methyl-25-cyclohexyl avermectin B2 5-oxime

This was prepared from 23-O-methyl-25-cyclohexyl avermectin B2 5-N,N-dimethylhydrazone (synthesized from 5-keto-23-O-methyl-25-cyclohexyl avermectin B2 according to the method of Example 1) via conversion to the 3-chloro-23-0-methyl-25-cyclohexyl avermectin B2 N,N-dimethylhydrazone, according to the method of Example 1. Oximation of this to the title compound was performed as described in Example 4. This was characterized by nmr and mass spectroscopy.

EXAMPLE 31

3-Bromo-22,23-dihydro-25-cyclohexyl avermectin B1 monosaccharide 5-N,N-dimethylhydrazone The hydrazone from Preparation A (200 mg) was dissolved in acetonitrile (50 ml), and stirred with 4A molecular sieve (1 g) for 1 hour. It was cooled to 0°, and N-bromosuccinimide (NBS) (45 mg) added portionwise over 1 hour. A further 10 mg of NBS was added, and the mixture stirred for a further 30 minutes. It was then poured into dilute aqueous sodium bisulphite solution, extracted with ethyl acetate, washed with water and brine, dried (MgSO$_4$) and evaporated. The product was purified by chromatography over silica gel (75 g) eluting with hexane:ether (3:2). Appropriate fractions were pooled and the product thus obtained. This was characterized by nmr and mass spectroscopy.

EXAMPLE 32

3-Bromo-22,23-dihydro-25-cyclohexyl avermectin B1 monosaccharide

This was prepared from the compound in Example 31 by conversion to the 3-bromo-5-ketone, and sodium borohydride reduction, as described in Example 7. It was characterized by nmr and mass spectroscopy.

EXAMPLE 33

3-Bromo-22,23-dihydro-25-cyclohexyl avermectin B1 monosaccharide 5-oxime

This was prepared from the compound in Example 31 by the oximation protocol described in Example 4. It was characterized by nmr and mass spectroscopy.

EXAMPLE 34

3-Vinyl-22,23-dihydro-25-cyclohexyl avermectin B1 monosaccharide 5-N,N-3dimethylhydrazone The 3-iodo-avermectin from Example 18 (150 mg) was dissolved in dimethylformamide (7.5 ml) and tri-n-butyl- vinylstannane (0.81 g) and tetrakis(triphenylphosphine) palladium(O) (~10 mg) added. The mixture was heated at 100° under nitrogen for 4 hours. The solvent was then removed under vacuum at room temperature and the resulting oil chromatographed over silica gel (50 g), eluting with ether:hexane (7:3). The title compound was obtained by pooling appropriate fractions (100 mg). It was characterized by nmr and mass spectroscopy.

EXAMPLE 35

3-Vinyl-22,23-dihydro-25-cyclohexyl avermectin B1 monosaccharide 5-oxime

This was prepared from the compound in Example 34 by the oximation protocol described in Example 4. The product was purified on a 1" Dynamax (TM) ODS column, eluting with methanol:water (9:1) at 18 ml/min. The product eluted after 26 minutes. It was characterized by nmr and mass spectroscopy.

EXAMPLE 36

3-Vinyl-5-keto-22,23-dihydro-25-cyclohexyl avermectin B1 monosaccharide

The hydrazone from Example 34 (70 mg) was dissolved in glacial acetic acid (7 ml) and saturated aqueous copper(II) acetate (1.4 ml) added. The mixture was stirred at 35° C. for 2 days. The reaction was evaporated and the product isolated by ether extraction. The ketone thus obtained was used directly in the next step.

EXAMPLE 37

3-Vinyl-22,23-dihydro-25-cyclohexyl avermectin B1 monosaccharide

The ketone from the previous Example (40 mg) was dissolved in methanol (40 ml), and treated with sodium borohydride (20 mg). The mixture was stood at room temperature for 15 minutes, then quenched by addition of 10% aqueous citric acid (1 ml). The product was extracted with ethyl acetate. The extracts were stripped and the residue chromatographed on silica gel (10 g), eluting with dichloromethane:ether 2:1. Avermectin-containing fractions were pooled, evaporated and purified by reverse-phase hplc. The title compound was characterized by nmr and mass spectroscopy.

EXAMPLE 38

3-Ethynyl-22,23-dihydro-25-cyclohexyl avermectin B1 monosaccharide 5-N,N-dimethylhydrazone The 3-iodo-avermectin from Example 18 (150 mg)was dissolved in dimethylformamide (7.5 ml) and ethynyl-tri-n-butyl stannane (0.75 ml) and tetrakis(triphenylphosphine) palladium(O) (~10 mg) added. The mixture was heated under nitrogen at 50° for 3 hours. The solvent was removed at room temperature under high vacuum, and the residue chromatographed over silica gel (50 g), eluting with ether:hexane (75:25). Fractions containing product were pooled. It was characterized by nmr and mass spectroscopy.

EXAMPLE 39

3-Ethynyl-22,23-dihydro-25-cyclohexyl avermectin B1 monosaccharide 5-oxime

This was obtained from the product from Example 38 by the oximation protocol of Example 4. It was characterized by nmr and mass spectroscopy.

EXAMPLE 40

3-Ethynyl-5-keto-22,23-dihydro-25-cyclohexyl avermectin B1 monosaccharide

The 3-ethynyl hydrazone from Example 38 (50 mg) was dissolved in DMF (dimethyl formamide) (5 ml), cooled to −42° C. m-Chloroperbenzoic acid (22 mg) was added, and the reaction warmed to −10° C. over 1 hour; this temperature was maintained for 1.5 hours, then the mixture was warmed to 0° C. for 20 minutes. The reaction was quenched in saturated aqueous sodium bicarbonate solution, extracted with ethyl acetate, washed with brine, dried (MgSO$_4$) and evaporated to give the product ketone as a yellow solid.

EXAMPLE 41

3-Ethynyl-22,23-dihydro-25-cyclohexyl avermectin B1 monosaccharide

The ketone from the previous Example (70 mg) was dissolved in methanol (10 ml), and treated with sodium borohydride (20 mg). The mixture was stood at room temperature for 20 minutes, and was then worked up as in Example 37. The crude product was purified by reverse-phase hplc on a 1" Microsorb (TM) ODS column, eluting with methanol:water 87:13 at 20 ml/min. The product obtained by pooling and evaporation of appropriate fractions was characterized by nmr and mass spectroscopy.

EXAMPLE 42

3-Azido-5-keto-23-O-methyl-25-cyclohexyl avermectin B2

The 3-chloro-ketone from Example 28 (100 mg) was stirred in acetonitrile (10 ml) at room temperature, and finely ground lithium azide (100 mg) added all in one lot. The mixture was briefly sonicated,and stirred at room temperature for 6 hours. Reaction was not yet complete, so the mixture was kept at −70° for 72 hours, allowed to reach room temperature for a further 3 hours, when all starting material had been consumed. The mixture was poured into water (100 ml) and extracted with ether (2×100 ml). The extracts were washed with water, then brine, dried (MgSO$_4$) and evaporated to a foam. This was characterized as the title azide by nmr, mass and infrared spectroscopy.

EXAMPLE 43

3-Azido-23-O-methyl-25-αcyclohexyl avermectin B2

The azido-ketone from the previous Example (50 mg) was dissolved in methanol (2 ml) and sodium borohydride (8 mg) added. After 10 minutes, the crude reaction mixture was chromatographed on a 1" Microsorb (TM) ODS column, eluting with methanol:water (86:14) at 18 ml/min. The material which eluted between 40 and 48 minutes was collected and shown to be the title azide by nmr, mass and infrared spectroscopy.

EXAMPLE 44

5-Keto-Milbemycin-UK-86,956

Milbemycin UK-86,956 (defined in U.S. Pat. No. 5,073, 567 and obtained by the process described therein) (10 g) was dissolved in a 3:1 mixture of ether:tetrahydrofuran (400 ml). Then manganese dioxide (10 g) was added with stirring. After 3 hours, a further 10 g of manganese dioxide was added, and the mixture stood at room temperature overnight. A further 10 g of manganese dioxide was then added, and the reaction stirred for 4 hours. The solution was filtered through Hyflo (TM), the residue washed well with ether, and the filtrate evaporated to give the product as a yellow solid.

EXAMPLE 45

Milbemycin-UK-86,956-5-N,N-dimethylhydrazone

This was prepared from the ketone of the preceding Example by the method of Preparation A.

EXAMPLE 46

3-Chloro-5-milbemycin-UK-86,956-N,N-dimethylhydrazone

The milbemycin 5-N,N-dimethylhydrazone from the previous Example (0.5 g) was dissolved in acetonitrile (100 ml) and stirred 10 minutes at room temperature with 4A molecular sieve (1 g). The mixture was then cooled to 0° C. in an ice/salt mixture, and N-chlorosuccinimide (2.8 g) was added. The mixture was stored at 0° C. for 24 hours, when tlc indicated a complete conversion. The reaction was then poured into aqueous sodium metabisulphite, extracted well with ether, and washed with water, and brine. It was dried (MgSO$_4$) and stripped to give a yellow solid. This was purified by reverse-phase hplc on a 2" Dynamax (TM) ODS column, eluting with methanol:water 90:10, at 40 ml/min, to give the title compound, characterized by nmr and mass spectroscopy.

EXAMPLE 47

3-Chloro-5-keto -milbemycin-UK-86,956

The 3-chloro-hydrazone from the previous Example (0.88 g) was dissolved in glacial acetic acid (50 ml), and saturated aqueous copper(II) acetate solution (25 ml) added, and the mixture heated to 35° C. overnight, when conversion was complete. It was then partitioned between water and ether, the extracts washed with water, dried (MgSO$_4$), and stripped to give the title compound as a yellow solid, characterized by mass spectroscopy.

EXAMPLE 48

3-Chloro-milbemycin-UK-86,956

The ketone from the previous Example (900 mg) was dissolved in methanol (30 ml) and sodium borohydride (200 mg) added in one portion. This was stirred for 15 minutes, then partitioned between water and ether (50 ml). The extracts were washed with water, dried (Na$_2$SO$_4$), and stripped to give crude product. This was purified by reverse-phase hplc on a 2" Dynamax (TM) ODS column, eluting with methanol:water 85:15 at 40 ml/min. Appropriate fractions were pooled to give the title compound, characterized by nmr and mass spectroscopy.

EXAMPLE 49

3-Bromo-5-milbemycin-UK-86,956-N,N-dimethylhydrazone

The milbemycin 5-N,N-dimethylhydrazone from Example 45 (1 g) was dissolved in acetonitrile (125 ml) and 4A molecular sieve (2 g) added. The mixture was then cooled to 0° C. in an ice/salt mixture, and N-bromosuccinimide (0.17 g) in acetonitrile (25 ml) was added over 30 minutes, then the mixture was stirred at 0° C. for 2 hours, when hplc indicated a complete conversion. The reaction was then poured into aqueous sodium metabisulphite, extracted well with ether, and washed with water, and brine. It was dried (MgSO$_4$) and stripped to give a yellow solid. This was purified by reverse-phase hplc on a 2" Dynamax (TM) ODS column, eluting with methanol:water 85:15, at 40 ml/min, to give the title compound, characterized by nmr and mass spectroscopy.

EXAMPLE 50

3-Bromo-5-keto-milbemycin-UK-86,956

The 3-bromo-hydrazone from the previous Example (0.2 g) was dissolved in glacial acetic acid (12 ml), and saturated aqueous copper(II) acetate solution (6 ml) added, and the mixture heated to 35° C. overnight, when conversion was complete. It was then partitioned between water and ether, the extracts washed with water, dried (MgSO$_4$), and stripped to give the title compound as a yellow solid.

EXAMPLE 51

3-Bromo-milbemycin-UK-86,956

The ketone from the previous Example (180 mg) was dissolved in methanol (6 ml) and sodium borohydride (40 mg) added in one portion. This was stirred for 15 minutes, then partitioned between water and ether (50 ml). The extracts were washed with water, dried (Na$_2$SO$_4$), stripped to give crude product. This was purified by reverse-phase hplc on a 1" Dynamax (TM) ODS column, eluting with methanol:water 85:15 at 40 ml/min. Appropriate fractions were pooled to give the title compound, characterized by nmr and mass spectroscopy.

EXAMPLE 52

3-Chloro-22,23-dihydro-avermectin B1a 5-N,N-dimethylhydrazone 22,23-Dihydro-avermectin B1a 5-N,N-dimethylhydrazone (prepared from the 5-ketone according to Preparation A) (2.8 g) was dissolved in acetonitrile (340 ml) and stirred 10 minutes at room temperature with 4A molecular sieve (8 g). The mixture was then cooled to 0° C. in an ice/salt mixture, and N-chlorosuccinimide (2.8 g) was added portionwise over 15 minutes. The mixture was stored at 0° C. for 24 hours, when tlc indicated a complete conversion. The reaction was then poured into aqueous sodium metabisulphite, extracted well with ether, and washed with water, and brine. It was dried (MgSO$_4$) and stripped to give a yellow solid. This was purified in two lots by reverse-phase hplc on a 2" Dynamax (TM) column, eluting with methanol:water 95:5, at 45 ml/min, to give the title compound, characterized by nmr and mass spectroscopy.

EXAMPLE 53

3-Chloro-5-keto-22,23-dihydro-avermectin B1 a

The 3-chloro-hydrazone from the previous Example (2.8 g) was dissolved in glacial acetic acid (100 ml), and saturated aqueous copper(II) acetate solution (50 ml) added, and the mixture heated to 35° C. overnight, when conversion was complete. It was then cooled, filtered and partitioned between water and ether, the extracts washed with water, dried (MgSO$_4$), and stripped to dryness. The residue was chromatographed over silica gel and eluted with ether, to give the title compound.

EXAMPLE 54

3-Chloro-2,2,23-dihydro-avermectin B1a

The ketone from the previous Example (500 mg) was dissolved in methanol (35 ml) and sodium borohydride (260 mg) added in one portion. This was stirred for 30 minutes, then partitioned between water and ether (50 ml). The extracts were washed with water, dried (Na$_2$SO$_4$), stripped to give crude product. This was purified by reverse-phase hplc on a 2" Dynamax (TM) ODS column, eluting with methanol:water 95:5 at 45 ml/min. Appropriate fractions were pooled to give the title compound, characterized by nmr and mass spectroscopy.

EXAMPLE 55

3-Chloro-22,23-dihydro-avermectin B1a monosaccharide

The product from the previous Example (300 mg) was dissolved in a 1% solution of concentrated sulphuric acid in isopropanol (2 ml), and left overnight. The mixture was diluted with water, and the mixture was extracted with ether. The extracts were washed water, dried (Na$_2$SO$_4$), and stripped to give a solid. This was purified by reverse-phase hplc on a 1" Dynamax (TM) ODS column, eluting 3.0 with methanol:water 90:10 at 9 ml/min. Appropriate fractions were pooled to give the title compound, characterized by nmr and mass spectroscopy.

EXAMPLE 56

3-Chloro.-22,23-dihydro-avermectin B1a 5-oxime

The hydrazone from Example 52 (2 g) was dissolved in a mixture of methanol and dioxan (1:1,400 ml). A solution of hydroxylammonium chloride (20 g) in water (100 ml) was added. After 24 hours, the mixture worked up as in Example 22. The crude solid was purified in two batches by reverse-phase hplc on a 2" Dynamax (TM) ODS column, eluting with methanol:water 90:10 at 40 ml/min. Fractions with retention time 10.8 minutes were pooled to give the title oxime, characterized by nmr and mass spectroscopy.

EXAMPLE 57

3-Chloro-22,23-dihydro-avermectin B1a monosaccharide 5-oxime

The product from the previous Example (300 mg) was hydrolysed to the monosaccharide using the sulphuric acid/isopropanol method of Example 54. The crude product was purified by reverse-phase hplc on a 1" Dynamax (TM) ODS column, eluting with methanol:water 90:10 at 9 ml/min. Fractions containing the product were pooled. The title compound was characterized by nmr and mass spectroscopy.

EXAMPLE 58

3-Chloro-22,23-dihydro avermectin B1a aglycone

The hydrolysis was conducted on crude disaccharide from Example 54 (300 mg). This was dissolved in a 1% solution of concentrated sulphuric acid in methanol (1 l), and left overnight. Workup was as in Example 54. The crude product was purified by reverse-phase hplc on a 2" Dynamax (TM) ODS column. Fractions containing the product were pooled. The title compound was characterized by nmr and mass spectroscopy.

EXAMPLE 59

3-Bromo-avermectin B1a 5-N,N-dimethylhydrazone

Avermectin B1a 5-N,N-dimethylhydrazone (prepared from the 5-ketone according to Preparation A) (0.5 g) was dissolved in acetonitrile (100 ml) and stirred 10 minutes at room temperature with 4A molecular sieve (1 g). The mixture was then cooled to −20° C. in an ice/salt mixture, and N-bromosuccinimide (0.11 g) was added portionwise over an hour. Tlc indicated a complete conversion. The reaction was then poured into aqueous sodium metabisulphite, extracted well with ether, and washed with water, and brine. It was dried ($MgSO_4$) and stripped to give a yellow solid. This was purified by reverse-phase hplc on a 2" Dynamax (TM) ODS column, eluting with methanol:water 85:15, at 40 ml/min, to give the title compound, characterized by nmr and mass spectroscopy.

EXAMPLE 60

3-Bromo-5-keto-avermectin B1a

The 3-bromo-hydrazone from the previous Example (0.99 g) was dissolved in glacial acetic acid (50 ml), and saturated aqueous copper(II) acetate solution (25 ml) added, and the mixture heated to 35° C. overnight, when conversion was complete. It was then partitioned between water and ether, the extracts washed with water, dried ($MgSO_4$), and stripped to dryness, to give the title compound as a yellow solid.

EXAMPLE 61

3-Bromo-avermectin B1a

The ketone from the previous Example (800 mg) was dissolved in methanol (30 ml) and sodium borohydride (200 mg) added portionwise. This was stirred for 20 minutes, then partitioned between water and ether (50 ml). The combined extracts were washed with water, dried, and stripped to give crude product. This was purified in two batches by reverse-phase hplc on a 2" Dynamax (TM) ODS column, eluting with methanol:water 85:15 at 40 ml/min. Appropriate fractions were pooled to give the title compound, characterized by nmr and mass spectroscopy.

EXAMPLE 62

3-Bromo-avermectin B1a monosaccharide

The product from the previous Example (400 mg) was dissolved in a 1% solution of concentrated sulphuric acid in isopropanol (400 ml), and left overnight. The mixture was diluted with water, and the mixture was extracted with ether. The extracts were washed with aqueous sodium bicarbonate, water, dried ($Na_2SO_4$), and stripped to give a solid. This was purified by reverse-phase hplc on a 2" Dynamax (TM) ODS column, eluting with methanol:water 85:15 at 40 ml/min. Appropriate fractions were pooled to give the title compound, characterized by nmr and mass spectroscopy.

EXAMPLE 63

3-Bromo-22,23-dihydro-avermectin B1a 5-N,N-dimethylhydrazone 22,23-Dihydro-avermectin B1a 5-N,N-dimethylhydrazone (prepared from the 5-ketone according to Preparation A) (6.66 g) was dissolved in acetonitrile (900 ml) and stirred 10 minutes at room temperature with 4A molecular sieve (24 g). The mixture was then cooled to 0° C. in an ice/salt mixture, and N-bromosuccinimide (1.42 g) in acetonitrile (100 ml) added dropwise over 15 minutes. The resulting red solution was stirred for a further 15 minutes, when tlc indicated a complete conversion. The reaction was then concentrated to ~100 ml, diluted with ethyl acetate (200 ml), and washed with aqueous sodium metabisulphite (100 ml of 5%), water, and brine. It was dried ($MgSO_4$) and stripped to give an orange foam. This was chromatographed over silica gel (250 g), eluting with dichloromethane:ethyl acetate 2:1, to give the title compound, characterized by nmr and mass spectroscopy.

EXAMPLE 64

3-Bromo-5-keto-22,23-dihydro-avermectin B1a

The bromo-hydrazone from the previous Example (4.5 g) was dissolved in glacial acetic acid (500 ml), and saturated aqueous copper(II) acetate solution (250 ml) added, and the mixture stirred at room temperature overnight. It was then heated to 45° for 4 hours, when conversion was complete. It was then cooled, filtered and stripped to dryness. The residue was partitioned between water (150 ml) and ether (150 ml). The aqueous phase was re-extracted with ether (1×100 ml) and the combined extracts washed with water (50 ml), aqueous potassium bicarbonate (50 ml), water (50 ml) and brine (20 ml), dried ($MgSO_4$), and stripped to dryness. The residue was chromatographed over silica gel (250 g) and eluted with dichloromethane:ethyl acetate 2:1, to give the title compound as a yellow foam, characterized by nmr and mass spectroscopy.

EXAMPLE 65

3-Bromo-22,23-dihydro-avermectin B1a

The ketone from the previous Example (500 mg) was dissolved in methanol (50 ml) and sodium borohydride (50 mg) added in one portion. This was stirred for 15 minutes, then stripped to low volume, partitioned between water (50 ml) and ether (50 ml). The aqueous phase was re-extracted with ether (1×50 ml), and the combined extracts washed water (2×20 ml), dried ($Na_2SO_4$), stripped and chromatographed over silica gel (80 g) eluting with dichloromethane:ethyl acetate 2:1, to give crude product. A portion (30 mg) was purified by reverse-phase hplc on a 1" Ultrasphere (TM) ODS column, eluting with methanol:water 90:10 at 5 ml/min. Appropriate fractions were pooled to give the title compound, characterized by nmr and mass spectroscopy.

EXAMPLE 66

3-Bromo-22,23-dihydro-avermectin B1a monosaccharide

The crude product from the previous Example (300 mg) was dissolved in a 1% solution of concentrated sulphuric acid in isopropanol (20 ml), and left overnight. The mixture was diluted with water (25 ml) and basified with saturated aqueous potassium bicarbonate (15 ml). The mixture was extracted with ether. The aqueous phase was re-extracted with ether, and the combined extracts washed water (2×10ml) and brine (10 mi), dried ($Na_2SO_4$), and stripped to give a gum. This was chromatographed over silica gel eluting with ether:hexane 4:1 to give crude product. This ws purified was purified by reverse-phase hplc on a 1" Phenomenex Primesphere (TM) ODS column, eluting with methanol:water 85:15 at 10 ml/min. Appropriate fractions were pooled to give the title compound, characterized by nmr and mass spectroscopy.

EXAMPLE 67

3-Bromo-22,23-dihydro-avermectin B1a aglycone

The hydrolysis was conducted on crude disaccharide from Example 65 (100 mg). This was dissolved in a 1% solution of concentrated sulphuric acid in methanol (20 ml), and left overnight. Workup as in the previous Example, and silica gel chromatography gave the title aglycone, characterized by nmr and mass spectroscopy.

EXAMPLE 68

22,23-dihydro-25-cyclohexyl avermectin B1 5-N,N-dimethylhydrazone

This was prepared from the 5-ketone, following the method of Preparation A.

EXAMPLE 69

3-Bromo-22,23-dihydro-25-cyclohexyl avermectin B1 5-N,N-dimethylhydrazone

The hydrazone from Example 68 (1.4 g) was dissolved in acetonitrile (240 ml), stirred with 4A molecular sieve (5 g) for 10 minutes, then cooled to 0° C. N-Bromosuccinimide (0.26 g) in acetonitrile (10 ml) was added dropwise over 30 minutes. A further portion of N-bromosuccinimide (50 mg) was added in acetonitrile (2 ml) over 10 minutes. The solution was filtered, and evaporated to 50 ml, diluted with ethyl acetate (200 ml), then washed with aqueous sodium metabisulphite and brine, dried ($MgSO_4$) and stripped to dryness. The solid was chromatographed over silica gel (100 g), eluting ether:hexane 1:1, rising to 3:2. Fractions containing the product were pooled to give the title compound, characterized by nmr and mass spectroscopy.

EXAMPLE 70

3-(4-Cyanophenyl)-22,23-dihydro-25-cyclohexyl avermectin B1 5-N,N-dimethylhydrazone 3-Bromo-22,23-dihydro-25-cyclohexyl avermectin B1 5-N,N-dimethylhydrazone (from Example 69) (150 mg) was heated with tri-n-butyl-(4-cyanophenyl)-stannane (0.5 ml) in dimethylformamide (8 ml) at 80° C., with tetrakis (triphenylphosphine)palladium(0) (10 mg) for 2 hours. The reaction was then evaporated to dryness, and the crude oil was chromatographed on silica gel, and eluted ether:hexane 7:3. The fractions containing the product were pooled and evaporated. The product was characterized by nmr and mass spectroscopy.

EXAMPLE 71

3-(4-Cyanophenyl)-5-keto-22,23-dihydro-25-cyclohexyl avermectin B1, and its monosaccharide derivative The hydrazone from the previous Example (70 mg) was dissolved in glacial acetic acid (8 ml) and saturated aqueous copper(II) acetate (2 ml) added. The mixture was stirred at 40° C. for 20 hours. The reaction was worked up as in Example 54, and the product—a mixture of the title compounds—was used directly in the next step.

EXAMPLE 72

3-(4-Cyanophenyl)-22,23-dihydro-25-cyclohexyl avermectin B1, and its monosaccharide derivative The mixture of ketones from Example 71 was dissolved in methanol (10 ml), and treated with sodium borohydride (10 mg). The mixture was stood at room temperature for 20 minutes, then quenched with aqueous citric acid. Workup as in Example 48 gave crude products, purified by reverse-phase hplc, eluting with methanol:water 85:15. The title monosaccharide eluted first, and followed by the title disaccharide. They were characterized by nmr and mass spectroscopy.

EXAMPLE 73

3-(2-Pyridyl)-22,23-dihydro-25-cyclohexyl avermectin B1 5-N,N-dimethylhydrazone

The 3-bromo-hydrazone from Example 69 (300 mg) was dissolved in dimethylformamide (15 ml) and 2-tri-n-butylstannylpyridine (1.5 ml) and tetrakis (triphenylphosphine)palladium(0) (60 mg) added. This mixture was stirred under nitrogen at 100° C. for 2.5 hours, then poured into water and extracted with ether. The organic phase ws washed with water and brine and dried ($MgSO_4$), and evaporated to give an oil. This ws chromatographed over silica gel (100 g), eluting with ether. Material of $R_f$ 0.2 was collected and shown to be the title compound by nmr and mass spectroscopy.

EXAMPLE 74

3-(2-Pyridyl)-22,23-dihydro-25-cyclohexyl avermectin B1 5-oxime

The hydrazone from Example 73 (75 mg) was dissolved in a mixture of methanol and dioxan (1:1, 16 ml). A solution of hydroxylammonium chloride (750 mg) in water (4 ml) was added. After 3 hours, the initial yellow colour had faded, and the mixture worked up as in Example 22. Chromatography over silica gel (70 g), eluting with ether, gave the title oxime, characterized by nmr and mass spectroscopy.

EXAMPLE 75

3-(2-Pyridyl)-22,23-dihydro-25-cyclohexyl avermectin B1 monosaccharide 5-oxime

The product from the previous Example (30 mg) was hydrolysed to the monosaccharide using the sulphuric acid/ isopropanol method of Example 55. The crude product was purified by reverse-phase hplc on a 1" Microsorb (TM) ODS column, eluting with methanol:water 86:14 at 20 ml/min. The product eluted at 21–25 minutes, and was characterized by nmr and mass spectroscopy.

EXAMPLE 76

3-Methyl-22,23-dihydro-25-cyclohexyl avermectin B1 5-N,N-dimethylhydrazone

The bromo-hydrazone from Example 69 (250 mg) was dissolved in dimethylformamide (12.5 ml) and tetramethyltin (1 ml) and tetrakis(triphenylphosphine)palladium(0) (20 mg) added. This mixture was stirred under nitrogen at 85° C. for 10 hours, then solvents were removed in vacuo, and the residue extracted with ether. The organic phase was washed with water and brine and dried ($MgSO_4$), and evaporated to give a gum. This was shown to be the title compound by nmr and mass spectroscopy.

EXAMPLE 77

3-Methyl-22,23-dihydro-25-cyclohexyl avermectin B1 5-oxime

The 3-methyl hydrazone from the previous Example (80 mg) was converted to the 5-oxime derivative by the method of Example 22. It was purified by chromatography over silica gel (70 g), eluting with ether:hexane 2:1, and was characterized by nmr and mass spectroscopy.

EXAMPLE 78

3-Methyl-22,23-dihydro-25-cyclohexyl avermectin B1 monosaccharide 5-oxime

The product from the previous Example (60 mg) was hydrolysed to the monosaccharide using the sulphuric acid/isopropanol method of Example 55. The crude product was purified by reverse-phase hplc on a 1" Microsorb (TM) ODS column, eluting with methanol:water 96:4 at 20 ml/min. The product eluted at 11–14 minutes, and was characterized by nmr and mass spectroscopy.

EXAMPLE 79

3-Methyl-5-keto-22,23-dihydro-25-cyclohexyl avermectin B1 monosaccharide

The 3-methyl hydrazone from Example 76 (156 mg) was dissolved in glacial acetic acid (25 ml) and a saturated aqueous solution of copper(II) acetate (10 ml) added. The mixture was stirred at room temperature for 24 hours, then heated to 45° C. for 4 hours, then at 30° C. for 24 hours. The solvents were then removed under vacuum, the solution neutralized with aqueous sodium bicarbonate solution, and the products extracted into ethyl acetate. The organic phase was washed with water and brine, dried ($MgSO_4$) and evaporated to give crude ketone.

EXAMPLE 80

3-Methyl-22,23-dihydro-25-cyclohexyl avermectin B1 monosaccharide

The crude ketone from the previous Example was dissolved in methanol (15 ml), and sodium borohydride (100 mg) added. The reaction was worked up as in Example 48. The crude product was purified by chromatography over silica gel (50 g), eluting with ether. Fractions containing material of $R_f$ 0.15–0.25 were collected and further purified by reverse-phase hplc on a 1" Microsorb (TM) ODS column, eluting with methanol:water 90:10 at 20 ml/min. The product eluted at 22–25 minutes, and was characterized by nmr and mass spectroscopy.

EXAMPLE 81

3-Bromo-25-cyclohexyl avermectin B2 5-N,N-dimethylhydrazone

25-Cyclohexyl avermectin B2 5-N,N-dimethylhydrazone was prepared from the corresponding ketone by the method of Preparation A. The hydrazone (2 g) was dissolved in acetonitrile (250 ml) and stirred with 4A molecular sieve (3 g) for 10 minutes. It was then cooled to 0° C., and N-bromosuccinimide (372 mg) in acetonitrile (50 ml) added over 30 minutes. the mixture was stirred at 0° C. for a further hour. It was then worked up as in Example 69, and the resulting crude gum chromatographed over silica gel (100 g), eluting with ether:hexane 3:1. The fractions containing material of $R_f$ 0.35 were pooled and evaporated to give the title bromo compound as a pale yellow solid, which was characterized by nmr and mass spectroscopy.

EXAMPLE 82

3-Bromo-25-cyclohexyl avermectin B2 5-oxime

The 3-bromo hydrazone from the previous Example (300 mg) was converted to the 5-oxime derivative by the method of Example 22. It was purified by chromatography over silica gel (100 g), eluting with ether, and collecting material of $R_f$ 0.25 on tlc. The oxime was characterized by nmr and mass spectroscopy.

EXAMPLE 83

3-Bromo-25-cyclohexyl avermectin B2 monosaccharide 5-oxime, and the corresponding aglycone The product from the previous Example (160 mg) was hydrolysed to the monosaccharide using the sulphuric acid/isopropanol method of Example 55. The crude product was purified by reverse-phase hplc on a 2" Microsorb (TM) ODS column, eluting with methanol:water 85:15 at 40 ml/min. The title aglycone eluted at 18.5 minutes, and the monosaccharide at 26–29 minutes. Both were characterized by nmr and mass spectroscopy.

EXAMPLE 84

3-Bromo-5-keto-25-cyclohexyl avermectin B2

The 3-bromo hydrazone from Example 81 (300 mg) was dissolved in glacial acetic acid (50 ml) and a saturated aqueous solution of copper(II) acetate (20 ml) added. The mixture was stirred at room temperature for 3 days. The solvents were then removed under vacuum, the solution neutralized with aqueous sodium bicarbonate solution, and the product extracted into ethyl acetate. The organic phase was washed with water and brine, dried ($MgSO_4$) and evaporated to give crude ketone.

EXAMPLE 85

3-Bromo-25-cyclohexyl avermectin B2

The crude ketone from the previous Example was dissolved in methanol (25 ml), and sodium borohydride (100 mg) added. Tlc showed reaction to be complete after 10 minutes. After addition of acetone (2 ml), the reaction was worked up as in Example 48. The crude product was purified by reverse-phase hplc on a 1" Microsorb (TM) ODS column, eluting methanol:water 85:15 at 19 ml/min. The product eluted at 22–30 minutes, and was characterized by nmr and mass spectroscopy.

EXAMPLE 86

3-Bromo-25-cyclohexyl avermectin B2 monosaccharide

The product from the previous Example (150 mg) was hydrolysed to the monosaccharide using the sulphuric acid/isopropanol method of Example 55. The crude product was purified by reverse-phase hplc on a 2" Microsorb (TM) ODS column, eluting methanol:water 85:15 at 38 ml/min. The title compound eluted at 25–28 minutes, and was characterized by nmr and mass spectroscopy.

EXAMPLE 87

3-Ethyl-22,23-dihydro-25-cyclohexyl avermectin B1 5-N,N-dimethylhydrazone

The 3-bromo-hydrazone from Example 69 (300 mg) was dissolved in dimethylformamide (14 ml) and tetraethyltin (1.25 ml) and tetrakis(triphenylphosphine)palladium(0) (25 mg) added. This mixture was stirred under nitrogen at 100° C. for 2 hours, then solvents were removed in vacuo, and the residue extracted with ether (50 ml). The organic phase was washed with water and brine and dried ($MgSO_4$), and evaporated to give a gum. This was chromatographed over silica gel (50 g), eluting with ether:hexane 2:1. The fractions containing product were pooled and evaporated to give the title compound as a pale yellow solid, which was characterized by nmr and mass spectroscopy.

EXAMPLE 88

3-Ethyl-22,23-dihydro-25-cyclohexyl avermectin B1 5-oxime

The 3-ethyl hydrazone from the previous Example (50 mg) was converted to the 5-oxime derivative by the method of Example 22. The crude product was purified by reverse-phase hplc on a 1" Microsorb (TM) ODS column, eluting with methanol:water 95:5 at 20 ml/min. The product eluted at 18–22 minutes, and was characterized by nmr and mass spectroscopy.

EXAMPLE 89

3-Ethyl-22,23-dihydro-25-cyclohexyl avermectin 81 monosaccharide 5-oxime

The product from the previous Example (50 mg) was hydrolysed to the monosaccharide using the sulphuric acid/isopropanol method of Example 55. The crude product was purified by reverse-phase hplc on a 1" Microsorb (TM) ODS column, eluting with methanol:water 90:10 for 10 minutes, then methanol:water 95:5 at 18 ml/min. The product eluted at 28–32 minutes, and was characterized by nmr and mass spectroscopy.

EXAMPLE 90

3-Ethyl-5-keto-22,23-dihydro-25-cyclohexyl avermectin B1a and its monosaccharide The 3-ethyl hydrazone from Example 87 (130 mg) was dissolved in glacial acetic acid (20 ml) and a saturated aqueous solution of copper(II) acetate (10 ml) added. The mixture was stirred and heated to 40° C. for 24 hours, then at room temperature for 72 hours. The mixture was then reheated to 40° C. for a further 24 hours.The solvents were then removed under vacuum, the residue partitioned between ether and water, and the ether solution neutralized with aqueous sodium bicarbonate soluition. The organic phase was washed with water and brine, dried ($MgSO_4$) and evaporated to give the crude ketones as a mixture.

EXAMPLE 91

3-Ethyl-22,23-dihydro-25-cyclohexyl avermectin B1 and its monosaccharide

The crude ketones from the previous Example were dissolved in methanol (15 ml), and excess sodium borohydride added. The reaction was worked up as in Example 48. The crude product was purified by reverse-phase hplc on a 1" Microsorb (TM) ODS column, eluting with methanol:water 90:10 at 20 ml/min. The monosaccharide eluted at 27–29 minutes, and the disaccharide at 43–48 3.0 minutes. Both materials were characterized by nmr and mass spectroscopy.

EXAMPLE 92

3-Bromo-25-cyclohexyl avermectin B1 5-N,N-dimethylhydrazone

25-Cyclohexyl avermectin B1 5-N,N-dimethylhydrazone was prepared from the corresponding ketone by the method of Preparation A. The hydrazone (29.9 g) was dissolved in acetonitrile (1 I) and stirred with 4A molecular sieve (10 g) for 30 minutes. It was then cooled to 0° C., and N-bromosuccinimide (5.95 g) in acetonitrile (100 ml) added over 60 minutes. Addition was stopped when a permanent red colour was seen in the solution. It was then worked up as in Example 69, and the resulting crude foam chromatographed over silica gel (500 g), eluting with ether:hexane 1:1. The fractions containing product were pooled and evaporated to give the title bromo compound as a pale yellow solid, which was characterized by nmr and mass spectroscopy.

EXAMPLE 93

3-Bromo-5-keto-25-cyclohexyl avermectin B1

The 3-bromo hydrazone from Example 92 (500 mg) was dissolved in glacial acetic acid (50 ml) and a saturated aqueous solution of copper(II) acetate (25 ml) added. The mixture was stirred at room temperature for 24 hours, and then heated to 45° C. for 6 hours. The solvents were then removed under vacuum, and the residue partitioned between ether and water, and the ether solution neutralized with aqueous sodium bicarbonate solution. The organic phase was washed with water and brine, dried ($MgSO_4$) and evaporated to give crude ketone.

EXAMPLE 94

3-Bromo-25-cyclohexyl avermectin B1

The crude ketone from the previous Example was dissolved in methanol (15 ml), and sodium borohydride (50 mg) added. Hplc showed reaction to be complete after 10 minutes. After addition of aqueous citric acid, the reaction was worked up as in Example 48. The crude product was purified by reverse-phase hplc on a 1" Microsorb (TM) ODS column, eluting with methanol:water 90:10 at 20 ml/min. The product eluted at 18–24 minutes, and was characterized by nmr and mass spectroscopy.

EXAMPLE 95

3-Bromo-25-cyclohexyl avermectin B1 monosaccharide

The product from the previous Example (150 mg) was hydrolysed to the monosaccharide using the sulphuric acid/isopropanol method of Example 55. The crude product was purified by reverse-phase hplc on a 2" Microsorb (TM) ODS column, eluting with methanol:water 88:12 at 40 ml/min. The title compound eluted at 24–27 minutes, and was characterized by nmr and mass spectroscopy.

EXAMPLE 96

3-Methyl-25-cyclohexyl avermectin B1 5-N,N-dimethylhydrazone

The bromo-hydrazone from Example 92 (500 mg) was dissolved in dimethylformamide (25 ml) and tetramethyltin (2 ml) and tetrakis(triphenylphosphine)palladium(0) (50 mg) added. This mixture was stirred under nitrogen at 85° C. for 1 hour, the reaction was poured into water, and extracted with ether. The organic phase was washed with water and brine and dried (MgSO$_4$), and evaporated to give a gum. The crude product was purified by chromatography over silica gel (80 g), eluting with ether:hexane 2:1. Fractions containing material of R$_f$ 0.5 were collected and shown to be the title compound by nmr and mass spectroscopy.

EXAMPLE 97

3-Methyl-5-keto-25-cyclohexyl avermectin B1 and its monosaccharide

The 3-methyl-hydrazone from the previous Example (300 mg) was dissolved in glacial acetic acid (35 ml) and a saturated aqueous solution of copper(II) acetate (17.5 ml) added. The mixture was stirred at room temperature for 24 hours, then heated to 50° C. for 12 hours. The solvents were then removed under vacuum, the residue partitioned between ether and water, the ether solution neutralized with aqueous sodium bicarbonate soluition. The organic phase was washed with water and brine, dried (MgSO$_4$) and evaporated to give the crude ketones as a mixture.

EXAMPLE 98

3-Methyl-25-cyclohexyl avermectin B1 and its monosaccharide

The crude ketones from the previous Example was dissolved in methanol (20 ml), and excess sodium borohydride added. The reaction was worked up as in Example 48. The crude product was purified by reverse-phase hplc on a 2" Microsorb (TM) ODS column, eluting with methanol:water 87:13, rising to methanol:water 90:10 after 30 minutes, at 42 ml/min. The monosaccharide eluted at 27 minutes, and the disaccharide at 43 minutes. Each compound was characterized by nmr and mass spectroscopy.

EXAMPLE 99

3-Bromo-23-O-methyl-25-cyclohexyl avermectin B2 5-N,N-dimethylhydrazone 1.5 23-O-methyl-25-cyclohexyl avermectin B2 5-N,N-dimethylhydrazone was prepared from the corresponding ketone by the method of Preparation A. The hydrazone (6 g) was dissolved in acetonitrile (500 ml) and stirred with 4A molecular sieve (10 g) for 30 minutes. It was then cooled to 0° C., and N-bromosuccinimide (1.2 g) in acetonitrile (250 ml) added over 60 minutes. The reaction was then worked up as in Example 69, and the resulting crude orange solid chromatographed over silica gel, eluting with ether:hexane 3:2 The fractions containing product were pooled and evaporated to give the title bromo compound as a pale yellow solid, which was characterized by nmr and mass spectroscopy.

EXAMPLE 100

3-Bromo-23-O-methyl-5-keto-25-cyclohexyl avermectin B2a nd its monosaccharide The 3-bromo hydrazone from the previous Example (500 mg) was dissolved in glacial acetic acid (25 ml) and a saturated aqueous solution of copper(II) acetate (5 ml) added. The mixture was heated to 40° C. for 20 hours. The solvents were then removed under vacuum, and the residue partitioned between ether and water, and the ether solution neutralized with aqueous sodium bicarbonate solution. The omgnic phase was washed with water and brine, dried (MgSO$_4$) and evaporated to give crude ketones.

EXAMPLE 101

3-Bromo-23-O-methyl-25-cyclohexyl avermectin B2 and its monosaccharide

The crude ketones from the previous Example were dissolved in methanol (50 ml), and sodium borohydride (50 mg) added. Reaction was complete after 10 minutes. After addition of aqueous citric acid, the reaction was worked up as in Example 48. The crude product was purified by reverse-phase hplc, eluting with methanol:water 88:12. The monosaccharide product eluted first, followed by the disaccharide. Both were characterized by nmr and mass spectroscopy.

EXAMPLE 102

3-Methyl-23-O-methyl -25-cyclohexyl avermectin B2 5-N,N-dimethylhydrazone

The bromo-hydrazone from Example 99 (300 mg) was dissolved in dimethylformamide (25 ml) and tetramethyltin (2 ml) and tetrakis(triphenylphosphine)palladium(0) (20 mg) added. This mixture was stirred under nitrogen at 80° overnight. Solvents were removed in vacuo, and the residue extracted with ether. The organic phase was washed with water and brine and dried (MgSO$_4$), and evaporated to give a yellow solid. This was shown to be the title compound by nmr and mass spectroscopy.

EXAMPLE 103

3-Methyl-5-keto-23-O-methyl-22,23-dihydro-25-cyclohexyl avermectin B1 and its monosaccharide The 3-methyl hydrazone from the previous Example (100 mg) was dissolved in glacial acetic acid (10 ml) and a saturated aqueous solution of copper(II) acetate (2 ml) added. The mixture was stirred at room temperature for 24 hours, then heated to 40° C. for 20 hours. The solvents were then removed under vacuum, the residue partitioned between ether and water, the ether solution neutralized with aqueous sodium bicarbonate soluition. The organic phase was washed with water and brine, dried (MgSO$_4$) and evaporated to give the crude ketones as a mixture.

EXAMPLE 104

3-Methyl-23-O-methyl-22,23-dihydro-25-cyclohexyl avermectin B1 and its monosaccharide The crude ketones from the previous Example were dissolved in methanol (20 ml), and excess sodium borohydride (50 mg) added. The reaction was worked up as in Example 48. The crude product was purified by reverse-phase hplc, eluting with methanol:water 85:15. The monosaccharide eluted first, followed by the disaccharide. Each compound was characterized by nmr and mass spectroscopy.

EXAMPLE 105

3-Allyl-22,23-dihydro-25-cyclohexyl avermectin B1 5-N,N-dimethylhydrazone

The bromo-hydrazone from Example 99 (300 mg) was dissolved in dimethylformamide (14 ml) and allyl-tri-n- butyltin (1.25 ml) and tetrakis(triphenylphosphine) palladium(0) (25 mg) added. This mixture was stirred under nitrogen at 100° C. for 4 hours, then solvents were removed in vacuo, and the residue extracted with ether (50 ml). The organic phase was washed with water and brine and dried (MgSO$_4$), and evaporated to give an oil. This was chromatographed over silica gel (50 g), eluting with ether:hexane 2:1. The fractions containing product were pooled and evaporated to give the title compound as a pale yellow solid, which was characterized by nmr and mass spectroscopy.

EXAMPLE 106

3-Allyl-22,23-dihydro-25-.cyclohexyl avermectin B1 5-oxime

The 3-allyl hydrazone from the previous Example (80 mg) was converted to the 5-oxime derivative by the method of Example 22. The crude product was purified by reverse-phase hplc on a 1" Microsorb (TM) ODS column, eluting with methanol:water 95:5 at 20 ml/min. The product eluted at 18–20 minutes, and was characterized by nmr and mass spectroscopy.

EXAMPLE 107

3-Allyl-22,23-dihydro-25-cyclohexyl avermectin B1 monosaccharide 5-oxime

The product from the previous Example (50 mg) was hydrolysed to the monosaccharide using the sulphuric acid/isopropanol method of Example 55. The crude product was purified by reverse-phase hplc on a 1" Microsorb (TM) ODS column, eluting with methanol:water 90:10 for 10 minutes, then methanol:water 95:5 at 18 ml/min. The product eluted at 27–31 minutes, and was characterized by nmr and mass spectroscopy.

EXAMPLE 108

3-Allyl-5-keto-22,23-dihydro-25-cyclohexyl avermectin B1 and its monosaccharide

The 3-allyl hydrazone from Example 105 (130 mg) was dissolved in glacial acetic acid (20 ml) and a saturated aqueous solution of copper(II) acetate (10 ml) added. The mixture was stirred and heated to 40° C. for 24 hours, then at room temperature for 72 hours. The mixture was then reheated to 40° C. for a further 24 hours.The solvents were then removed under vacuum, the residue partitioned between ether and water, the ether solution neutralized with aqueous sodium bicarbonate solution. The organic phase was washed with water and brine, dried (MgSO$_4$) and evaporated to give crude ketones as a mixture.

EXAMPLE 109

3-Allyl-22,23-dihydro-25-cyclohexyl avermectin B1 and its monosaccharide

The crude ketones from the previous Example were dissolved in methanol (15 ml), and excess sodium borohydride added. The reaction was worked up as in Example 48. The crude product was purified by reverse-phase hplc on a 1" Microsorb (TM) column, eluting with methanol:water 90:10 at 20 ml/min. The monosaccharide eluted at 25–28 minutes, and the disaccharide at 38–43 minutes. Both materials were characterized by nmr and mass spectroscopy.

EXAMPLE 110

3-Methoxymethyl-22,23-dihydro-25-cyclohexyl avermectin B1 5-N,N-dimethylhydrazone 3-Bromo-22,23-dihydro-25-cyclohexyl avermectin B1 5-N,N-dimethylhydrazone (from Example 69) (150 mg) was heated with tri-n-butyl-methoxymethyl-stannane (1 ml) in dimethylformamide (5 ml) at 80° C., with tetrakis (triphenylphosphine)palladium(0) (10 mg) for 4 hours. The reaction was evaporated to a black oil. This was chromatographed on silica gel and eluted ether:hexane 1:1. The product was further purified by reverse-phase hplc eluting with methanol:water 95:5. Fractions containing product were pooled and evaporated to give the title compound. The product was characterized by nmr and mass spectroscopy.

EXAMPLE 111

3-Methoxymethyl-5-keto-22,23-dihydro-25-cyclohexyl avermectin B1 and its monosaccharide The hydrazone from the previous Example (60 mg) was dissolved in glacial acetic acid (7 ml) and a saturated aqueous solution of copper(II) acetate (1.4 ml) added. The mixture was stirred and heated to 40° C. for 20 hours. The solvents were then removed under vacuum, the residue partitioned between ether and water, the ether solution neutralized with aqueous sodium bicarbonate solution. The organic phase was washed with water and brine, dried (MgSO$_4$) and evaporated to give crude ketone as a yellow solid.

EXAMPLE 112

3-Methoxymethyl-22,23-dihydro-25-cyclohexyl avermectin B1 and its monosaccharide The crude ketones from the previous Example were dissolved in methanol (10 ml), and excess sodium borohydride (10 mg) added. The reaction was worked up as in Example 48. The crude product was purified by reverse-phase hplc, eluting with methanol:water 85:15. The 3-methoxymethylmonosaccharide eluted first, followed by the 3-methoxymethyldisaccharide. The two products were characterized by nmr and mass spectroscopy.

EXAMPLE 113

3-Ethynyl-22,23-dihydro-25-cyclohexyl avermectin B1-5-N,N-dimethylhydrazone

This was prepared from the 3-bromo-hydrazone from Example 69 and tri-n-butyl-ethynylstannane, using the method of Example 38.

EXAMPLE 114

3-(1-Acetoxyvinyl)-22,23-dihydro-25-cyclohexyl avermectin B1-5-N,N-dimethylhydrazone The 3-ethynyl-hydrazone from the previous Example (70 mg) was dissolved in a mixture of glacial acetic acid (5 ml), water (2 ml), tetrahydrofuran (2 ml) and sodium acetate (1 g). The mixture was stirred at room temperature for 3 hours. The reaction was poured into water (200 ml) and the product isolated by extraction with ethyl acetate. The extracts were washed with water, then brine, dried (MgSO$_4$) and evaporated to a yellow solid. The title product thus obtained was characterized by nmr and mass spectroscopy, and used directly in the next step.

EXAMPLE 115

3-(1-Acetoxyvinyl)-22,23-dihydro-25-cyclohexyl avermectin B1-5-oxime

The hydrazone from the previous Example (80 mg) was dissolved in a mixture of methanol (12 ml) and dioxan (12 ml), and treated with a solution of hydroxylammonium chloride (500 mg) in water (6 ml). After 20 hours, the mixture was worked up as in Example 22. The crude product was purified by reverse-phase hplc on a 1" Dynamax (TM) ODS column, eluting with methanol:water 90:10 at 20 ml/min. Pooling and evaporation of appropriate fractions gave the title oxime, characterized by nmr and mass spectroscopy.

EXAMPLE 116

3-(1-Ethoxyvinyl)-22,23-dihydro-25-cyclohexyl avermectin B1 5-N,N-3,5-dimethylhydrazone 3-Bromo-22,23-dihydro-25-cyclohexyl avermectin B1 5-N,N-dimethylhydrazone (from Example 69) (200 mg) was heated with tri-n-butyl-(1-ethoxyvinyl)-stannane (1 ml) in dimethylformamide (8 ml) at 80° C., with tetrakis (triphenylphosphine)palladium(0) (20 mg) for 4 hours. The reaction was evaporated to a black oil. This was chromatographed on silica gel and eluted ether:hexane 3:2. Fractions containing product were pooled and evaporated to give the title olefin as a yellow solid. The product was characterized by nmr and mass spectroscopy.

EXAMPLE 117

3-Acetyl-22,23-dihydro-25-cyclohexyl avermectin B1 5-oxime

The hydrazone from the previous Example (80 mg) was converted to the 5-oxime derivative by the method of Example 22. The crude product was purified by reverse-phase hplc. The product was characterized by nmr and mass spectroscopy.

EXAMPLE 118

3-Acetyl-22,23-dihydro-25-cyclohexyl avermectin B1 monosaccharide 5-oxime

The product from the previous Example (150 mg) was hydrolysed to the monosaccharide using the sulphuric acid/isopropanol method of Example 55. The crude product was purified by reverse-phase hplc, eluting with methanol:water 95:5. The title compound was characterized by nmr and mass spectroscopy.

EXAMPLE 119

3-(1-Ethoxyvinyl)-5-keto-22,23-dihydro-25-cyclohexyl avermectin B1

The 3-ethoxyvinyl hydrazone from Example 116 (50 mg) was dissolved in dimethylformamide (5 ml), cooled to −42° C. m-Chloroperbenzoic acid (30 mg) was added, and the reaction warred to −5° C. over 1 hour. The reaction was quenched in saturated aqueous sodium bicarbonate solution, extracted with ethyl acetate, washed with brine, dried (MgSO₄) and evaporated to give the product ketone as an orange oil.

EXAMPLE 120

3-(1-Ethoxyvinyl)-22,23-dihydro-25-cyclohexyl avermectin B1

The crude ketone from the previous Example was dissolved in methanol (10 ml), and excess sodium borohydride (20 mg) added. The reaction was worked up as in Example 48. The crude product was purified by reverse-phase hplc on a 1" Microsorb (TM) ODS column, eluting with methanol:water:acetonitrile 13:10:77 at 20 ml/min. The product obtained by pooling and evaporation of appropriate fractions was characterized by nmr and mass spectroscopy.

EXAMPLE 121

3-(1-Ethoxyvinyl)-22,23-dihydro-25-cyclohexyl avermectin B1 monosaccharide 5-N,N-dimethylhydrazone 3-Iodo-22,23-dihydro-25-cyclohexyl avermectin B1 monosaccharide 5-N,N-dimethylhydrazone (from Example 19) (200 mg) was heated with tri-n-butyl-(1-ethoxyvinyl)-stannane (1 ml) in dimethylformamide (10 ml) at 80° C., with tetrakis(triphenylphosphine)palladium(0) (20 mg) for 4 hours. The reaction was evaporated to a black oil. This was chromatographed on silica gel and eluted ether:hexane 3:2. Fractions containing product were pooled and evaporated to give the title olefin as a yellow solid. The product was characterized by nmr and mass spectroscopy.

EXAMPLE 122

3-(1-Ethoxyvinyl)-5-keto-22,23-dihydro-25-cyclohexyl avermectin B1 monosaccharide The 3-ethoxyvinyl hydrazone from Example 121 (50 mg) was dissolved in dimethylformamide (5 ml), cooled to −42° C. m-Chloroperbenzoic acid (30 mg) was added, and the reaction warmed to −10° C. for 3 hours. The reaction was quenched in aqueous sodium metabisulphite, and saturated aqueous sodium bicarbonate solution, extracted with ethyl acetate, washed with brine, dried (MgSO₄) and evaporated to give the product ketone as an yellow oil.

EXAMPLE 123

3-Acetyl-22,23-dihydro-25-cyclohexyl avermectin B1 monosaccharide

The crude ketone from the previous Example was dissolved in methanol (10 ml), and excess sodium borohydride (20 mg) added. The reaction was worked up as in Example 48. The crude product was purified by reverse-phase hplc on a 1" Microsorb (TM) ODS column, eluting with methanol:water:acetonitrile 13:10:77 at 20 ml/min. The product obtained by pooling and evaporation of appropriate fractions was characterized by nmr and mass spectroscopy.

EXAMPLE 124

3-(1-Methoxycarbonylvinyl)-22,23-dihydro-25-cyclohexyl avermectin B1 5-N,N-dimethylhydrazone 3-Bromo-22,23-dihydro-25-cyclohexyl avermectin B1 5-N,N-dimethylhydrazone (from Example 69) (150 mg) was heated with tri-n-butyl-(1-methoxycarbonylvinyl)-stannane (1 ml) in dimethylformamide (5 ml) at 80° C., with tetrakis (triphenylphosphine)palladium(0) (20 mg) for 2 hours. The reaction was evaporated to a black oil. This was chromatographed on silica gel and eluted ether:hexane 7:3. Fractions containing product were pooled and evaporated to give the title olefin as a yellow solid. The product was characterized by nmr and mass spectroscopy.

EXAMPLE 125

3-(1-Methoxycarbonylvinyl)-5-keto-22,23-dihydro-25-cyclohexyl avermectin B1 and its monosaccharide The 3-vinyl hydrazone from the previous Example (70 mg) was dissolved in glacial acetic acid (7 ml) and a saturated aqueous solution of copper(II) acetate (1.4 ml) added. The mixture was stirred and heated to 40° C. for 20 hours. The solvents were then removed under vacuum, the residue partitioned between ether and water, the ether solution neutralized with aqueous sodium bicarbonate solution. The organic phase was washed with water and brine, dried (MgSO$_4$) and evaporated to give crude ketone as a yellow oil.

EXAMPLE 126

3-(1-Methoxycarbonylvinyl)-22,23-dihydro-25-cyclohexyl avermectin B1 and its monosaccharide, and 3-(1-Methoxycarbonylethyl)-22,23-dihydro-25-cyclohexyl avermectin B1 and its monosaccharide The crude ketones from the previous Example were dissolved in methanol (10 ml), and excess sodium borohydride (20 mg) added. The reaction was worked up as in Example 48. The crude product was purified by reverse-phase hplc on a 1" Microsorb (TM) ODS column, eluting with methanol:water 85:15. The 3-(1-methoxycarbonylvinyl)monosaccharide eluted first, then the 3-(1-methoxycarbonylethyl)monosaccharide, followed by the 3-(1-methoxycarbonylvinyl)disaccharide, and the 3-(1-methoxycarbonylethyl)disaccharide. All four products were characterized by nmr and mass spectroscopy.

EXAMPLE 127

3-(2-Methoxycarbonylvinyl)-22,23-dihydro-25-cyclohexyl avermectin B1 5-N,N-dimethylhydrazone 3-Bromo-22,23-dihydro-25-cyclohexyl avermectin B1 5-N,N-dimethylhydrazone (from Example 69) (150 mg) was heated with tri-n-butyl-(1-methoxycarbonylvinyl)-stannane (1.5 ml) in dimethylformamide (5 ml) at 80° C., with tetrakis(triphenylphosphine)palladium(0) (20 mg) for 2 hours. The reaction was evaporated to a black oil. This was chromatographed on silica gel and eluted ether:hexane 7:3. Fractions containing product were pooled and evaporated to give the title olefin as a yellow solid. The product was characterized by nmr and mass spectroscopy.

EXAMPLE 128

3-(2-Methoxycarbonylvinyl1)-5-keto-22,23-dihydro-25-cyclohexyl avermectin B1 and its monosaccharide The 3-vinyl hydrazone from Example 127 (70 mg) was dissolved in glacial acetic acid (7 ml) and a saturated aqueous solution of copper(II) acetate (1.4 ml) added. The mixture was stirred and heated to 40° C. for 20 hours. The solvents were then removed under vacuum, the residue partitioned between ether and water, the ether solution neutralized with aqueous sodium bicarbonate solution. The organic phase was washed with water and brine, dried (MgSO$_4$) and evaporated to give crude ketones as a yellow oil.

EXAMPLE 129

3-(2-Methoxycarbonylvinyl)-22,23-dihydro-25-cyclohexyl avermectin B1 monosaccharide The crude ketones from the previous Example were dissolved in methanol (10 ml), and excess sodium borohydride (20 mg) added. The reaction was worked up as in Example 48. To complete the hydrolysis, the sulphuric acid/isopropanol method of Example 55 was employed. The crude product was purified by reverse-phase hplc, eluting with methanol:water 85:15. The product was characterized by nmr and mass spectroscopy.

EXAMPLE 130

3-[1-(t-Butyl-dimethylsilyloxymethyl)vinyl]-22,23-dihydro-25-cyclohexyl avermectin B1 5-N,N-dimethylhydrazone 3-Bromo-22,23-dihydro-25-cyclohexyl avermectin B1 5-N,N-dimethylhydrazone (from Example 69) (150 mg) was heated with tri-n-butyl-[1-(t-butyl-dimethylsilyloxymethyl) vinyl]-stannane (1 ml) in dimethylformamide (5 ml) at 80° C., with tetrakis(triphenylphosphine)palladium(0) (20 mg) for 2 hours. The reaction was evaporated to a black oil. This was chromatographed on silica gel and eluted ether:hexane 7:3. Fractions containing product were pooled and evaporated to give the title olefin as a yellow solid. The product was characterized by nmr and mass spectroscopy.

EXAMPLE 131

3-[1-(Hydroxymethyl)oxiranyl]-5-keto-22,23-dihydro-25-cyclohexyl avermectin B1

The 3-vinyl hydrazone from the previous Example (70 mg) was dissolved in dimethylformamide (5 ml), cooled to −42° C. m-Chloroperbenzoic acid (40 mg) was added, and the reaction warmed to −10° C. for 1.5 hours. The reaction was quenched in aqueous sodium metabisulphite, and saturated aqueous sodium bicarbonate solution, extracted with ethyl acetate, washed with brine, dried (MgSO$_4$) and evaporated to give the product ketone as an yellow oil.

EXAMPLE 132

3-[1-(Hydroxymethyl)oxiranyl]-22,23-dihydro-25-cyclohexyl avermectin B1

The crude ketone from the previous Example was dissolved in methanol (10 ml), and excess sodium borohydride (20 mg) added. The reaction was worked up as in Example 48. The crude product was purified by reverse-phase hplc, eluting with methanol:water 90:10. The product was characterized by nmr and mass spectroscopy.

EXAMPLE 133

3-(1-Cyanovinyl)-22,23-dihydro-25-cyclohexyl avermectin B1 5-N,N-dimethylhydrazone 3-Bromo-22,23-dihydro-25-cyclohexyl avermectin B1 5-N,N-dimethylhydrazone (from Example 69) (200 mg) was heated with tri-n-butyl-(1-cyanovinyl)-stannane (1 ml) in dimethylformamide (10 ml) at 80° C., with tetrakis (triphenylphosphine)palladium(0) (20 mg) for 4 hours. The reaction was evaporated to a black oil. This was chromatographed on silica gel and eluted ether:hexane 7:3. Fractions containing product were pooled and evaporated to give the title olefin. The product was characterized by nmr and mass spectroscopy.

EXAMPLE 134

3-(1-Cyanovinyl)-5-keto-22,23-dihydro-25-cyclohexyl avermectin B1 and its monosaccharide The 3-vinyl hydrazone from the previous Example (70 mg) was dissolved in glacial acetic acid (8 ml) and a saturated aqueous solution of copper(II) acetate (2 ml) added. The mixture was stirred at room temperature for 24 hours, then heated to 40° C. for 12 hours, then was stirred at room temperature for 48 hours. The solvents were then removed under vacuum, the residue partitioned between ether and water, the ether solution neutralized with aqueous sodium bicarbonate solution. The organic phase was washed with water and brine, dried (MgSO₄) and evaporated to give crude ketone as a yellow solid.

EXAMPLE 135

3-(1-Cyanovinyl)-22,23-dihydro-25-cyclohexyl avermectin B1 and its monosaccharide The crude ketones from the previous Example were dissolved in methanol (10 ml), and excess sodium borohydride (10 mg) added. The reaction was worked up as in Example 48. The crude product was purified by reverse-phase hplc on a 1" Microsorb (TM) column, eluting with methanol:water 85:15. The 3-(1-cyanovinyl) monosaccharide eluted first, then the 3-(1-cyanovinyl) disaccharide. The products were characterized by nmr and mass spectroscopy.

EXAMPLE 136

3-Phenyl-22,23-dihydro-25-cyclohexyl avermectin B1 5-N,N-dimethylhydrazone

3-Bromo-22,23-dihydro-25-cyclohexyl avermectin B1 5-N,N-dimethylhydrazone (from Example 69) (300 mg) was heated with tri-n-butyl-phenyl-stannane (0.5 ml) in dimethylformamide (7 ml) at 100° C., with tetrakis (triphenylphosphine)palladium(0) (60 mg) for 3 hours. The reaction was poured into water, and extracted with ether (2×100 ml), the extracts washed with water and brine, dried and evaporated to give a gum. This was chromatographed on silica gel (90 g), and eluted dichloromethane:ether 3:1. The fractions containing the product were pooled and evaporated. The product was characterized by nmr and mass spectroscopy.

EXAMPLE 137

3-Phenyl-5-keto-22,23-dihydro-25-cyclohexyl avermectin B1, and its monosaccharide derivative The hydrazone from the previous Example (60 mg) was dissolved in glacial acetic acid (5 ml) and saturated aqueous copper(II) acetate (2 ml) added. The mixture was stirred at room temerature overnight, then at 40° C. for 24 hours. The reaction was worked up as in Example 55, and the product—a mixture of the title compounds—was used directly in the next step.

EXAMPLE 138

3-Phenyl-22,23-dihydro-25-cyclohexyl avermectin B1, and its monosaccharide derivative The mixture of ketones from Example 139 was dissolved in methanol (5 ml), and treated with sodium borohydride (20 mg). The mixture was stood at room temperature for 20 minutes. Workup as in Example 48 gave crude products, chromatographed on silica gel (10 g), eluting with dichloromethane:ether 2:1. The fractions containing avermectins were further purified by reverse-phase hplc on a 1' Microsorb (TM) column, eluting with methanol:water 90:10 at 20 ml/min. The title monosaccharide eluted first at 23.1 minutes, followed by the title disaccharide at 37 minutes. They were characterized by nmr and mass spectroscopy.

EXAMPLE 139

3-Chloro-22,23-dihydro-25-cyclohexyl avermectin B1 monosaccharide 5-N,N-dimethylhydrazone 22,23-Dihydro-25-cyclohexyl avermectin B1 monosaccharide 5-N,N-dimethylhydrazone, made by the method of Preparation A (2.8 g) was dissolved in acetonitrile (70 ml) kept at between −150° and −10°. To this solution was added dropwise with stirring over a period of 20 minutes, a solution of N-chlorobenzotriazole (600 mg) in acetonitrile (10 ml). The mixture was kept at −10° for 1 hour then diluted with ether (150 ml), washed with 2% w/v sodium bisulphite solution (50 ml), water (50 ml), and brine (50 ml) and dried (MgSO₄). Evaporation gave a foam which was chromatographed over silica gel (125 g) and eluted with ether:hexane 1:2. Appropriate fractions were collected and pooled, and evaporated to give the title product (1.4 g).

EXAMPLE 140

3-Chloro-5-keto-22,23-dihydro-25-cyclohexyl avermectin B1 monosaccharide

The 3-chloro-hydrazone made by the method of the previous Example (2.75 g) was dissolved in glacial acetic acid (150 ml) and to this was added a saturated aqueous solution of copper (II) acetate (60 ml). The mixture was maintained at a temperature of 40° for 24 hours, then the solvents removed by rotary evaporation. The residue was suspended in water (150 ml) and extracted twice with ether (2×150 ml). The combined ether extracts were washed twice with saturated aqueous sodium bicarbonate solution (2×100 ml), brine (100 ml), dried (MgSO₄) and evaporated to give a foam.

We claim:
1. A compound of formula (1):

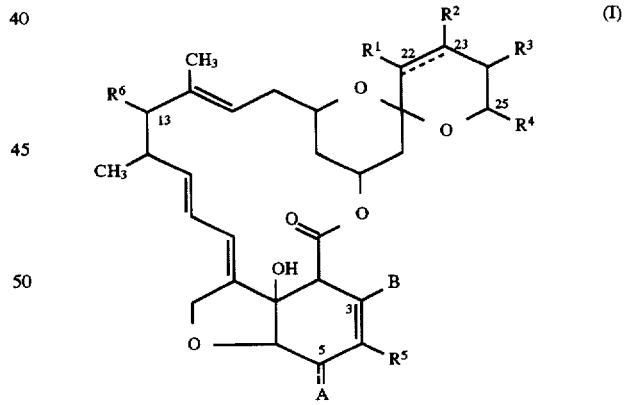

wherein the broken lines represent independently optional bonds, $R^1$ and $R^2$ being absent when the $C_{12}$–$C_{13}$ double bond is present, A is OH, halo, $C_1$–$C_8$ alkoxy, $C_1$–$C_9$ alkanoyloxy, oxo, or oximino optionally substituted by a $C_1$–$C_8$ alkyl, alkenyl, alkynyl, aryl, trialkyisilyl, aralkyl, $C_1$–$C_9$ alkanoyl group or other group capable of being hydrolysed in vivo to the oxime, or hydrazono optionally substituted by at least one $C_1$–$C_8$ alkyl, alkenyl, alkynyl, aryl, trialkylsilyl, aralkyl, $C_1$–$C_9$ alkoxycarbonyl, carbamoyl, thiocarbamoyl, aroyl or $C_1$–$C_9$ alkanoyl group, B is halo, $C_1$–$C_8$ alkyl, $C_1$–$C_8$ alkenyl, $C_1$–$C_8$ alkynyl, aryl, heteroaryl, $C_1$–$C_8$ alkanoyl, $C_1$–$C_8$ alkoxy, $C_1$–$C_9$ alkanoyloxy, $C_1$–$C_9$ alkoxycarbonyl, carboxy, arylcarbonyl, heteroaryl-carbonyl, mercapto, alkylthio, alkenylthio, arylthio, alkanoylthio, heteroarylthio, nitro, haloalkyl such as trifluoromethyl, hydroxyalkyl, alkoxyalkyl, mercaptoalkyl, alkylthio-alkyl, aminoalkyl optionally N-mono-or disubstituted by $C_1$–$C_8$ alkyl, $C_1$–$C_8$ alkenyl, $C_1$–$C_8$ alkynyl, $C_1$–$C_8$ alkanoyl, aryl, heteroaryl, $C_1$–$C_9$ alkoxycarbonyl, carboxy, arylcarbonyl, or by heteroarylcarbonyl, or B is hydroseleno, alkylseleno, arylseleno, heteroarylseleno, azido or B is cyclic ether group having up to 8 carbon atoms, said group optionally being substituted by at least one substituent selected from cyano, $C_1$–$C_8$ alkoxy, $C_1$–$C_8$ hydroxyalkyl, $C_1$–$C_9$ alkoxycarbonyl, aminocarbonyl, $C_1$–$C_9$ alkanoyl, arylcarbonyl, heteroarylcarbonyl, halo, haloalkyl and trialkylsilyloxyalkyl;

$R^1$ is H, OH, halo, oxo, $C_{1-8}$ alkoxy, $C_{1-9}$ alkanoyloxy, =$CH_2$ or oximino optionally 0-substituted by a $C_{1-8}$ alkyl, alkenyl, alkynyl, trialkylsilyl, aryl or aralkyl group $R^2$ is H, OH, halo, oxo, $C_{1-8}$ alkoxy optionally substituted by halo or by $C_{1-4}$ alkoxy, $C_{1-5}$ alkanoyl, $C_{1-5}$ alkoxycarbonyl, carboxy, mercapto or by aryl, or $R^2$ is $C_{3-8}$ alkenyloxy, $C_{1-9}$ alkylcarbonyloxy, $C_{3-9}$ alkenylcarbonyloxy, arylcarbonyl, carbamoyl optionally substituted by $C_{1-9}$ alkyl, or oximino optionally 0-substituted by a $C_{1-8}$ alkyl, alkenyl, alkynyl, trialkylsilyl, aryl or aralkyl group, or is methylene optionally substituted by a cyano or $C_{1-9}$ alkyl group;

$R^3$ is H or $C_{1-6}$ alkyl, $R^4$ is (a) an alpha-branched $C_3$–$C_8$ alkyl, alkenyl (including but-2-enyl, pent-2-enyl, and 4-methylpent-2-enyl), alkoxy-alkyl, or alkylthioalkyl group; an alpha-branched $C_4$–$C_8$ alkynyl group; a ($C_4$–$C_8$) cycloalkyl-alkyl group wherein the alkyl group is an alpha-branched $C_1$–$C_5$ alkyl group; a $C_3$–$C_8$ cycloalkyl or $C_5$–$C_8$ cycloalkenyl group, either of which may optionally be substituted by methylene or one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms; or (b) a group of the formula —$CH_2R^8$ wherein $R^8$ is H, $C_1$–$C_8$ alkyl, $C_1$–$C_8$ alkenyl, $C_1$–$C_8$ alkynyl, alkoxyalkyl or alkylthioalkyl containing from 1 to 6 carbon atoms in each alkyl or alkoxy group, wherein any of said alkyl, alkoxy, alkenyl or alkynyl groups may be substituted by one or more halo atoms; or a $C_3$–$C_8$ cycloalkyl or $C_5$–$C_8$ cycloalkenyl group, either of which may optionally be substituted by methylene or one or more $C_1$–$C_4$ alkyl groups or halo atoms; or a 3 to 6 membered oxygen or sulphur containing heterocyclic ring which may be saturated, or partially unsaturated and which may optionally be substituted by one or more $C_1$–$C_4$ alkyl groups or halo atoms; or a group of the formula $SR^9$ wherein $R^9$ is $C_1$–$C_8$ alkyl, $C_1$–$C_8$ alkenyl, $C_3$–$C_8$ alkynyl, $C_3$–$C_8$ cycloalkyl, $C_5$–$C_8$ cycloalkenyl, phenyl or substituted phenyl wherein the substituent is $C_1$–$C_4$ alkyl, $C_1$–$C_4$ alkoxy or halo; or a 3 to 6 membered oxygen or sulphur containing heterocylic ring which may be saturated, or fully or partially unsaturated and which may optionally be substituted by one or more $C_1$–$C_4$ alkyl groups or halo atoms; or (c) a $C_1$–$C_6$ alkyl group substituted by one oxo or one or more hydroxy groups or by a single oxygen atom on two adjacent carbon atoms forming an oxirane ring, or $R^4$ is a $C_1$–$C_5$ alkyl group substituted by a ($C_1$–$C_6$) alkoxy-carbonyl group, said substituents on $R_4$ being attached to either or both of a terminal carbon atom and a carbon atom adjacent a terminal carbon atom of R4; or (d) =$CH_2$ or a group of the formula:

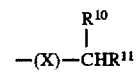

wherein $R^{10}$ and $R^{11}$ are both H; $R^{10}$ is H and $R^{11}$ is $C_1$–$C_3$ alkyl, or one of $R^{10}$ and $R^{11}$ is H and the other is phenyl, heteroaryl, $C_1$–$C_6$ alkoxycarbonyl or substituted phenyl or heteroaryl wherein said substituent is fluorine, chlorine, $C_1$–$C_4$ alkyl, $C_1$–$C_4$ alkoxy, $C_1$–$C_4$ alkylthio, hydroxy ($C_1$–$C_4$)alkyl, cyano, aminosulphonyl, $C_1$–$C_6$ alkanoyl, $C_1$–$C_6$ alkoxycarbonyl, nitro, trifluoromethyl, trifluoromethoxy, amino or mono or di($C_1$–$C_4$) alkylamino; and X is a direct bond or is an alkylene group having from 2 to 6 carbon atoms which may be straight or branched-chain; or (e) phenyl which may optionally be substituted with at least one substituent selected from $C_1$–$C_4$ alkyl, $C_1$–$C_4$ alkylthio groups, halo atoms, trifluoromethyl, and cyano;

or $R^4$ may be a group of formula (II):

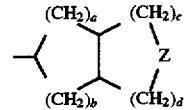

wherein Z is O, S or —$CH_2$— and a, b, c and d may each independently be 0, 1 or 2; the sum of a, b, c, and d not exceeding 5; $R^5$ is methyl, hydroxymethyl, ($C_1$–$C_4$ alkoxy)-methyl, ($C_1$–$C_5$ alkanoyl) oxymethyl, ($C_1$–$C_8$ alkenoyl)-oxymethyl, aroyloxymethyl, aralkanoyloxymethyl, formyl, optionally substituted oximino, halomethyl, azidomethyl or cyanomethyl, $R^6$ is hydrogen, hydroxy, $C_1$–$C_8$ alkoxy or alkenoxy, $C_1$–$C_9$ alkanoyloxy or alkenoyloxy, aroyloxy, oxymethyleneoxy-($C_1$–$C_5$)alkyloxy-($C_1$–$C_5$)alkyl, $C_1$–$C_9$ alkoxyalkoxy, halogen, oxo, or optionally substituted oximino, hydrazono, carbazido or semicarbazido, N-($C_1$–$C_4$)alkyl semicarbazido, N,N-di($C_1$–$C_4$) alkylsemicarbazido, $C_1$–$C_5$ alkanoylhydrazido, benzoylhydrazido or ($C_1$–$C_4$) alkyl benzoylhydrazido; or $R^6$ is a group capable of being hydrolysed in vivo to give OH; or $R^6$ is

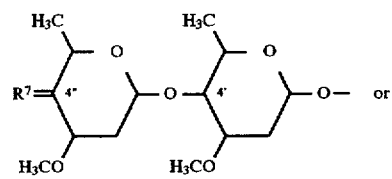

43

-continued

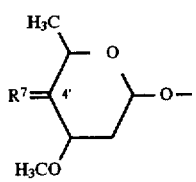

wherein R⁷ is attached to C-4" or C-4' by a single bond and is hydroxy, $C_1$–$C_9$ alkanoyloxy or alkenoyloxy, aroyloxy, $C_1$–$C_8$ alkoxy, amino, N-($C_1$–$C_8$)alkylamino, N,N-di($C_1$–$C^9$)alkylamino, N-($C_1$–$C_5$)alkanoylamino, or N,N-di($C_1$–$C^9$) alkanoylamino; or R⁷ is attached to C-4" or C-4' by a double bond and is oxo, optionally substituted oximino, semicarbazido, N-($C_1$–$C_4$) alkylsemicarbazido, N,N-di($C_1$–$C_4$ alkylsemicarbazido, ($C_1$–$C_5$)alkanoylhydrazido, benzoylhydrazido, or ($C_1$–$C_4$) alkylbenzoylhydrazido;

or R⁷ is a group capable of being hydrolysed in vivo to give OH.

2. A compound according to claim 1 in which the $C_{12}$–$C_{13}$ double bond is present or absent and R² is H, OH, O—($C_1$–$C_4$) alkyl, O—($C_1$–$C_5$) alkanoyl, oxo or oximino optionally substituted by $C_1$–$C_4$ alkyl or aryl ($C_1$–$C_4$) alkyl;

R² is straight or branched-chain alkyl, alkenyl, cycloalkyl or cycloalkenyl (including methyl, ethyl, 2-propyl, 2-butyl, 2-buten-2-yl, 2-penten-2-yl, 4-methyl-2-penten-2-yl and cyclohexyl); R¹ is H, OH, oxo or oximino; and R¹ is H or is of formula:

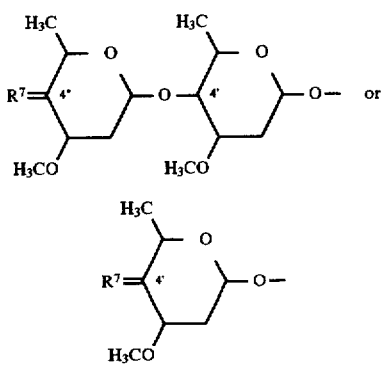

where R⁷ is OH, ($C_1$–$C_4$) alkoxy, ($C_1$–$C_5$) alkanoyloxy, amino, N—($C_1$–$C_4$) alkylamino, N—($C_1$–$C_5$) alkanoylamino, oxo or oximino optionally substituted by a $C_1$–$C_4$ alkyl group.

3. A compound according to claim 1, in which B is halo, alkyl, alkoxyalkyl, acyloxyalkenyl or acyl.

4. A compound according to claim 1, in which R¹ is H and R² is H, OH or methoxy and the $C_{12}$–$C_{13}$ double bond is absent, or in which the $C_{12}$–$C_{13}$ double bond is present, and R³ and R⁵ are methyl.

5. A compound according to claim 4, in which A is OH or oximino.

6. A compound according to claim 5, in which R⁶ is H, fluoro, oleandrosyl- or oleandrosyl-oleandrosyloxy or methoxymethoxy.

7. A compound according to claim 6, where B is Cl, Br or I.

44

8. A compound according to claim 7 where B is Cl or Br, and R⁴ is branched alkyl, alkenyl, cycloalkyl or cycloalkenyl (including 2-propyl, 2-butyl, 2-butenyl, 2-pentenyl, 4-methyl-2-penten-2-yl and cyclohexyl).

9. A compound according to claim 2 in which B is halo, alkyl, alkoxyalkyl, acyloxyalkenyl or acyl.

10. A pharmaceutical or veterinary composition, comprising a compound according to claim 1 and a pharmaceutically acceptable carrier or excipient.

11. A process for preparing a compound according to claim 1, which comprises:

(a) allowing a compound of formula (I) but in which B is H and A is =O to react with hydrazine optionally substituted by at least one $C_1$–$C_8$ alkyl, alkenyl, aryl, trialkylsilyl, aralkyl, $C_1$–C9 alkoxycarbonyl, carbamoyl, thiocarbamoyl, aroyl or $C_1$–$C_9$ alkanoyl group to yield a compound of formula (I) in which A is optionally substituted hydrazono, (b) allowing the hydrazone so obtained to react with source of electrophilic species E⊕ where E⊕ is Cl⊕, Br⊕, I⊕, NO₂⊕, ArS⊕ or ArSe⊕ where Ar is an aryl group or E⊕ is an iminium ion to yield a compound of formula (I) in which B is Cl, Br, I, NO₂, ArS, ArSe or an optionally substituted aminoalkyl group respectively, (c) if desired, allowing the compound produced from (b) in which B is Cl, Br or I to react with a stannane comprising an optionally substituted alkyl, alkenyl, alkynyl, aryl or heterocyclic substituent, in the presence of a catalyst such as triphenylphosphine palladium, to give a compound of formula (I) in which B is an optionally substituted alkyl, alkenyl, alkynyl, aryl or heterocyclic substituent respectively, (d) if desired, allowing the compound produced from (b) in which B is Cl, Br or I to react with an azide to produce a compound of formula (I) in which B is N₃.

(e) if desired, oxidising a compound from (c) in which B is alkenyl to produce a compound of formula (I) in which B is a cyclic ether group.

(f) if desired, treating a compound from (b) in which B is ArS or ArSe with a thiol or hydroselenide other than ArSH or ArSeH to produce a compound of formula (I) in which B is a mercapto or hydro selenide group, and if desired allowing the product to react with an alkyl, alkenyl, aryl, alkanoyl or heteroaryl halide.

12. A process according to claim 11, in which said source of electrophilic species is N-chlorosuccinimide or N-chlorobenzotriazole when E⊕ is Cl⊕, N-iodosuccinimide when E⊕ is I⊕ or N-bromosuccinimide when E⊕ is Br⊕, tetranitromethane when E⊕ is NO₂⊕, dinitrophenylsulphenyl chloride with E⊕ is ArS⊕, N-phenylselenophthalimide when E⊕ is ArSe⊕ or Me₂NCH₂Cl when E⊕ is an iminiuim ion.

13. A process according to claim 11, in which the hydrazone of formula (I) produced is allowed to react with optionally O-substituted hydroxylamine to produce a compound in which A is an optionally O-substituted oxime.

14. A process according to claim 11, in which the hydrazone of formula (I) produced is hydrolysed to a compound of formula I in which A is =O, and if desired the compound obtained is reduced to a compound in which A is —OH.

15. A process according to claim 11, in which a compound of formula (I) in which R⁶ is 4'-(α-L oleandrosyl)-α-L- oleandrosyloxy is hydrolysed to a compound in which $R^6$ is —OH or α-L-oleandrosyloxy.

16. A process according to claim 11 in which a compound of formula (I) having a double bond between the 22- and 23-positions is reduced to a compound in which $R^6$ and $R^2$ are both H.

17. A process according to claim 12 in which the hydrazone of formula (I) produced is allowed to react with optionally O-substituted hydroxylamine to produce a compound in which A is an optionally O-substituted amine.

18. A process according to claim 12 in which the hydrazone of formula (I) produced is hydrolysed to a compound of formula (I) in which A is =O, and if desired the compound obtained is reduced to a compound in which A is —OH.

19. A method of treating a mammal suffering from flea infestation comprising treating said mammal with an effective amount of a compound of claim 1 or a pharmaceutical composition thereof.

20. A method of treating a mammal suffering from a parasitic infection comprising treating said mammal with a parasite treating effective amount of a compound according to claim 1 or a pharmaceutical composition thereof.

* * * * *